(12) United States Patent
Turner

(10) Patent No.: US 7,677,890 B2
(45) Date of Patent: Mar. 16, 2010

(54) DENTAL HANDPIECE

(75) Inventor: Derek Turner, Ottawa (CA)

(73) Assignee: TTI Turner Technology Instruments Inc., Ottawa, Ontario (CA)

( * ) Notice: Subject to any disclaimer, the term of this patent is extended or adjusted under 35 U.S.C. 154(b) by 52 days.

(21) Appl. No.: 10/539,741

(22) PCT Filed: Dec. 22, 2003

(86) PCT No.: PCT/CA03/01999

§ 371 (c)(1),
(2), (4) Date: Jan. 19, 2006

(87) PCT Pub. No.: WO2004/056279

PCT Pub. Date: Jul. 8, 2004

(65) Prior Publication Data

US 2006/0121413 A1    Jun. 8, 2006

(30) Foreign Application Priority Data

Dec. 20, 2002    (CA) .................................... 2414908

(51) Int. Cl.
*A61C 1/14* (2006.01)
(52) U.S. Cl. ...................... 433/127; 433/128
(58) Field of Classification Search ................ 433/114, 433/127, 132, 128; 604/167–168, 170, 173, 604/180; 415/904
See application file for complete search history.

(56) References Cited

U.S. PATENT DOCUMENTS 1,984,663 A    12/1934    Tatham (Continued)

FOREIGN PATENT DOCUMENTS

CH    686 113    1/1996

(Continued)

OTHER PUBLICATIONS

Examiner's First Report Dated Mar. 18, 2008 From Australian Government, IP Australia.

*Primary Examiner*—Cris L Rodriguez
*Assistant Examiner*—Hao D Mai
(74) *Attorney, Agent, or Firm*—Clark Hill PLC

(57) ABSTRACT

A dental handpiece is disclosed including a turbine construction creating a radial in flow of air onto the impeller blades about the whole circumference of the turbine. This generates additional torque and avoids asymmetrical thrust on the impeller wheel. A pair of axially spaced air bearings support the turbine. Air supply to the bearings is controlled in such a way that the air bearings are floated before drive air is supplied to the turbine and after drive air to the turbine has been shut off. This ensures that the air bearings are always operational irrespective of the operational state of the turbine. The handpiece has an improved ergonomic shape, especially the shape and configuration of the front or drive head, which provides additional tooth clearance and a better field of view. An angled swivel connection to the umbilical cord is provided which reduces physical strain on the dentist's wrist. A self adjusting lock and key type torque connection between the dental burr and the chuck is provided which accommodates both conventional burrs and the burr of the lock and key arrangement. An auto stop arrangement for the turbine is disclosed which prevents a vacuum buildup during run-down of the turbine. The specific construction of the auto stop valve in accordance with the invention closes both the drive and exhaust air conduits.

15 Claims, 18 Drawing Sheets

U.S. PATENT DOCUMENTS

| | | | | |
|---|---|---|---|---|
| 2,791,835 A | * | 5/1957 | Staunt | 433/128 |
| 3,906,635 A | | 9/1975 | Lares et al. | |
| 4,014,099 A | | 3/1977 | Bailey | |
| 4,279,597 A | * | 7/1981 | Grimm | 433/129 |
| 4,370,132 A | | 1/1983 | Wohlgemuth | |
| 4,470,813 A | | 9/1984 | Thorburn | |
| 4,595,363 A | | 6/1986 | Nakanishi | |
| 4,820,154 A | | 4/1989 | Romhild et al. | |
| 5,000,684 A | * | 3/1991 | Odrich | 433/125 |
| 5,011,408 A | * | 4/1991 | Nakanishi | 433/127 |
| 5,057,015 A | | 10/1991 | Fleer | |
| 5,275,558 A | | 1/1994 | Seney | |
| 5,507,642 A | | 4/1996 | Wohlgemuth | |
| 5,549,474 A | | 8/1996 | Cohen | |
| 5,584,689 A | | 12/1996 | Loge | |
| 5,782,634 A | | 7/1998 | Lingenhole et al. | |
| 5,924,865 A | | 7/1999 | Quinn | |
| 6,033,220 A | | 3/2000 | Mosimann | |
| 6,065,966 A | | 5/2000 | Lohn et al. | |
| 6,120,291 A | | 9/2000 | Bareth et al. | |
| 6,305,935 B1 | * | 10/2001 | Cardarelli | 433/126 |
| 6,319,003 B2 | | 11/2001 | Mosimann | |
| 2001/0002975 A1 | | 6/2001 | Hashimoto et al. | |
| 2004/0161723 A1 | | 8/2004 | Helfenbein | |

FOREIGN PATENT DOCUMENTS

| | | |
|---|---|---|
| EP | 0 925 762 | 6/1999 |
| WO | WO 02/076308 | 10/2002 |

* cited by examiner

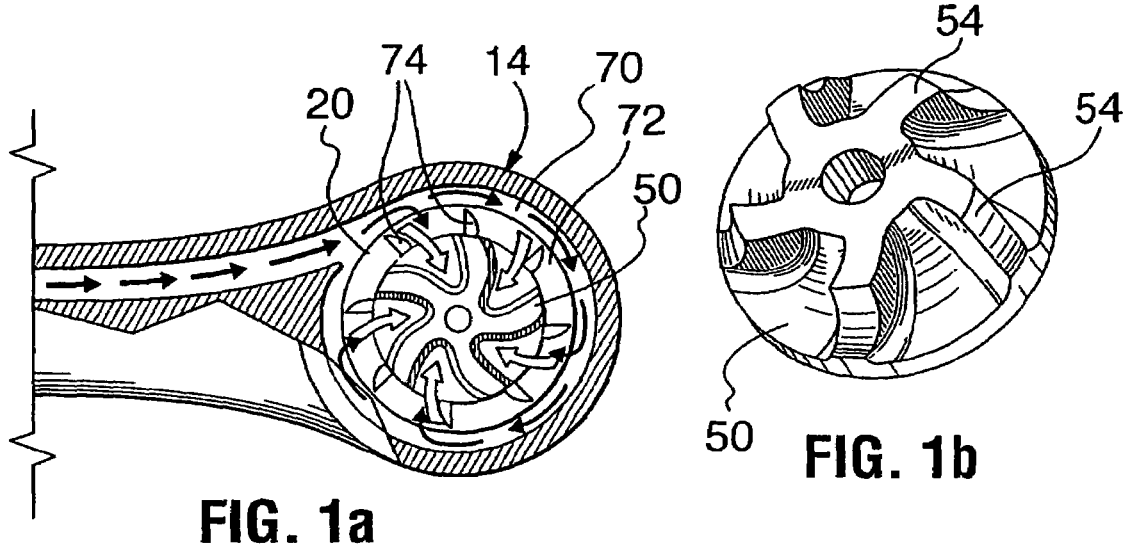
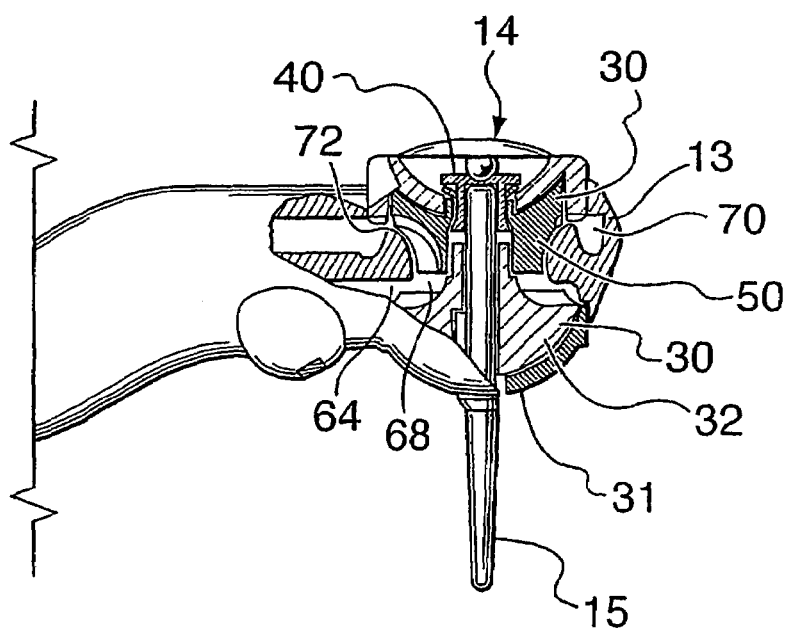

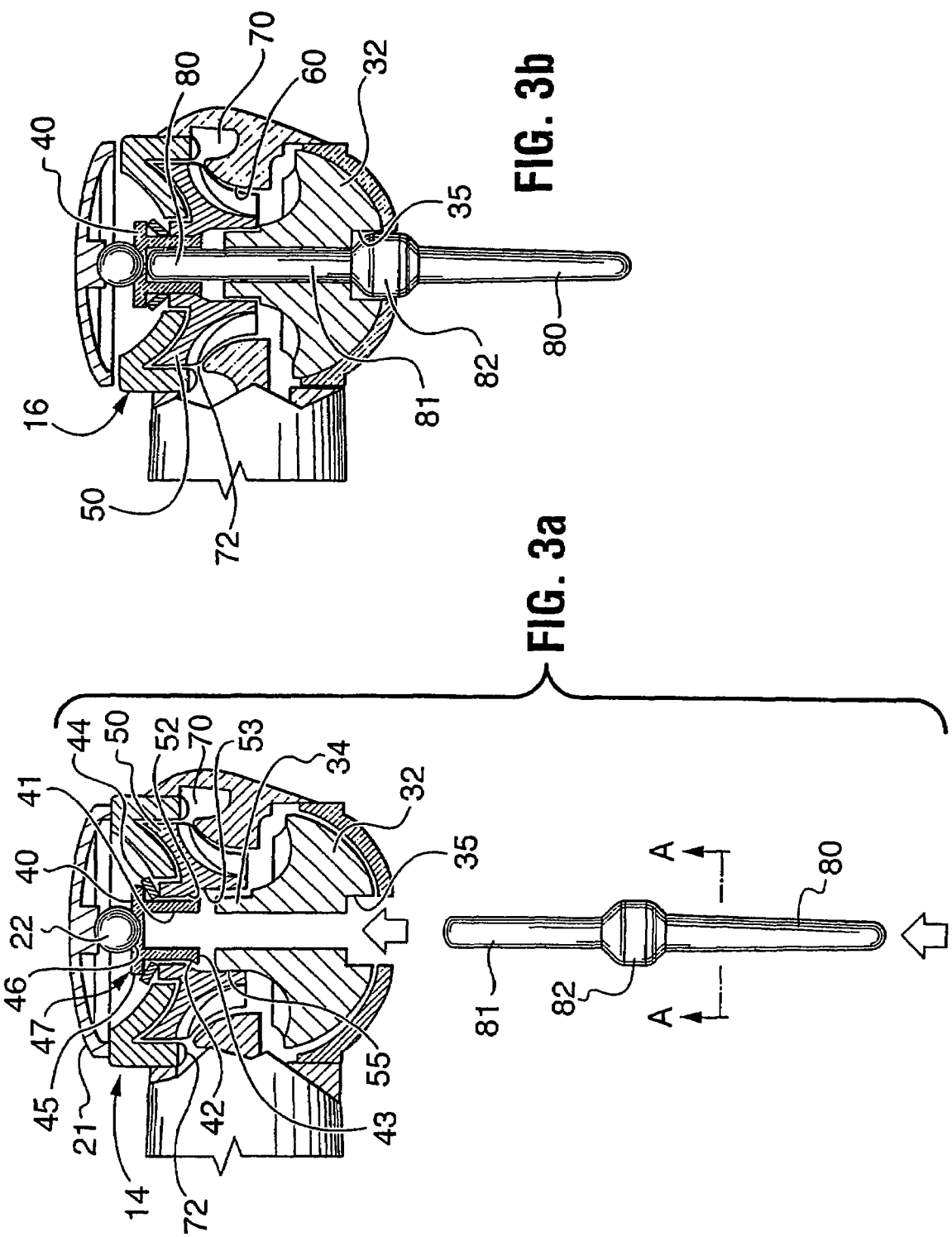

DENTAL HANDPIECE

This application is the National Stage of International Application No. PCT/CA03/01999, filed Dec. 22, 2003.

FIELD OF THE INVENTION

The present invention relates to handpieces for rotating tools and particularly to turbine driven medical or dental handpieces.

BACKGROUND OF THE INVENTION

Numerous handpieces for rotating tools exist. Turbine driven handpieces are widely used in dental offices and medical labs around the world. Most handpieces include a handle portion, a connector at one end of the handle portion and a tool carries drive head at the other end. The connector provides a connection of the handpiece to various air, water, light and power supply conduits, generally combined in a so called umbilical cord. The drive head houses a tool rotating assembly, generally composed of a tool mount or chuck, and a motor or a turbine turbine, rotatably mounted in the head for driving the chuck.

Various different types of turbine arrangements are in use, all of which include a turbine in a turbine housing, a supply of pressurized air into the housing for driving the turbine and a set of bearings for rotatably supporting the turbine in the housing and the head. Since conventional dental handpieces are constructed to rotate the dental drill or burr at speeds of up to 500,000 rpm, the bearings are subject to large stress. This is exaggerated by the bearings having to additionally support the chuck and tool against the lateral forces applied to the tool during operation. Furthermore, asymmetrical thrust generated by drive air impinging tangentially on the turbine places additional stress on the bearings.

In existing handpieces, mostly ball bearings are used, which generally have a maximum service life of 3 months and must be lubricated each time they are subjected to sterilization conditions. Ceramic bearings have come on the market recently which are more robust and are maintenance free in that they do not need to be lubricated after each sterilization. However, their service life is still not satisfactory.

U.S. Pat. No. 3,906,635 is directed to a dental handpiece with air bearings. In that handpiece, a central spindle supporting the turbine wheel and having an axial, burr receiving bore is supported in the drive head of the handpiece by a pair of cylindrical bearing sleeves which are closely spaced from the spindle, forming a very narrow air passage or air gap therebetween. The bearing sleeves are respectively mounted in a pressure chamber to which pressurized drive air is supplied. The bearing sleeves each include a number of air passages allowing pressurized air to pass from the pressure chamber into the air gap between the spindle and the bearing sleeve. The drive air is supplied simultaneously to the turbine and the air bearings. The pressurized drive air supporting the spindle enters into the bearing chambers, passes through the bearing sleeves and into the air passages, and from there gets exhausted to ambient or into the turbine chamber. It is easily apparent that operating the air bearings and the turbine with the same drive air causes a major disadvantage. At shut down of the drive air, the turbine still rotates while the air pressure is no longer sufficient to fully support the spindle in the bearing sleeves. This can result in serious damage to the bearing, which in turn limits the service life of the turbine drive unit. Moreover, although the cylindrical air cushions may properly support the spindle in radial direction, very little support in axial direction is provided. Axial thrust washers are provided in this prior art construction, which support the spindle in axial direction. Although annular air cushions are provided around the thrust washers, the overall surface of these air cushions appears to be quite small considering the potentially large axial thrust force applied to the spindle upon contact of the burr with a tooth. Furthermore, the sharp angle at the transition from the cylindrical air cushion to the annular air cushion impedes the flow of cushioning air. Thus, an improved bearing design is desired.

Many different air turbine designs and constructions exist, but in common turbine designs drive air is tangentially blown onto the impeller wheel of the turbine and at the circumference of the wheel. The tangential air supply generates asymmetrical thrust and causes asymmetrical loading of the bearings, which increases stress and wear. Furthermore, the torque generation of the turbine is low due to the only localized drive air supply. Moreover, parasitic airflow (drag) is high when the drive air is supplied tangentially at the circumference of the turbine.

Numerous air turbine designs are known in the prior art, wherein a paddle wheel type turbine rotor is driven by drive air impacting onto the turbine vanes at the outer ends thereof and in a direction tangential to the turbine circumference. Representative of the prior art designs are U.S. Pat. No. 6,120,291 and US Patent Application US 2001/0002975. Although U.S. Pat. No. 4,470,813 discloses an air driven turbine arrangement wherein the drive air is somewhat redirected radially before impact onto the turbine wheel, the drive air is still directed onto the turbine vanes in one location and in a generally tangential direction. Thus, a need exists for an improved turbine construction generating higher torque output and less bearing stress.

Prior art chucks of dental handpieces are almost exclusively designed to hold the dental burr by way of a friction fit only. Examples of such constructions are found in U.S. Pat. Nos. 4,595,363, 5,549,474, and 5,275.558. Only low torque transmission is possible between the chuck and the burr in such constructions, higher torque leading to slippage of the burr. In U.S. Pat. No. 6,065,966, a spring loaded pin is used for engaging a recess in a dental tool. However, the use of this arrangement in an air turbine handpiece is not disclosed. In fact, the disclosed arrangement could not be used to hold a dental burr, since the engagement between the pin and the chuck is designed for a non-rotating tool and does not easily lend itself to being used with a rotating tool.

A lock and key type connection is known from U.S. Pat. No. 4,370,132 which teaches the use of a burr with a shank having a flattened end portion at the upper shank end. A dog rigidly connected with the burr receiving sleeve is provided for engagement with the flattened end of the burr shank. The burr cannot be fully inserted into the chuck until the burr end fits into the dog, so that the burr must be turned relative to the chuck until these interlocking portions align. It is a disadvantage of this prior art arrangement that the burr must be rotated in the chuck until the lock and key structures fit together. Since the chuck also provides a friction fit with the burr, rotating the almost completely inserted burr within the chuck would necessitate some kind of mechanism which keeps the chuck from rotating in the drive head, or the burr must be repeatedly removed and reinserted in a slightly different angular position. Locating the interlocking mechanism deep in the drive head of the handpiece makes it impossible for the user to visually pre-align the lock and key structure prior to insertion of the burr. Thus, insertion of the burr is an exercise of trial and error.

Dental handpiece air turbines are normally shut down by simply stopping the supply of pressurized drive air. However, since the turbine is rotating at high speed, it takes some time to gradually slow down and come to a stop. This is undesirable, since for safety reasons, the dentist must wait until the turbine has fully stopped before removing the handpiece from a patient's mouth. Furthermore, during this so called rundown period, the continued rotation of the turbine generates a vacuum in the turbine chamber which may lead to contaminants being sucked into the chamber.

U.S. Pat. No. 5,507,642 discloses a discharge air shut-off arrangement for a dental handpiece turbine unit, which automatically prevents the flow of discharge air through the lower bearing during rundown of the turbine in order to prevent the generation of a vacuum. This is achieved by using a flexible Belleville washer which is held in a flat configuration by the drive air and automatically curves upward when the drive air is shut off, thereby closing off the air discharge passage. U.S. Pat. No. 5,782,634 discloses an auto-stop arrangement which includes a valve in the exhaust air conduit which is operated by the drive air pressure and closes the exhaust air conduit when the drive air pressure falls below a certain level. However, the valve arrangements of these two patents shut off only the exhaust air conduit, not the drive air and chip air/water conduits. Thus, a vacuum may still be generated and contamination may still occur. Consequently, a mechanism is desired which provides for a reliable and quick stopping of the turbine and prevents contamination of the turbine chamber as much as possible.

Dental turbine handpieces generally include either a straight neck or a bent neck, the latter intended to facilitate access to the back of a patient's teeth. However, the tooth clearance achievable with such a construction is limited by the length of the burr. For some situations, a better tooth clearance is desired. Furthermore, the treatment field is usually partially obstructed during use by the drive head and the neck. U.S. Pat. Nos. 1,984,663 and 4,820,154 respectively disclose a dental handpiece with an adjustable neck angle and a dental instrument (scaler) with a neck portion including two bends. Thus, a handpiece neck portion design is desired which provides additional tooth clearance and improved visibility of the field of treatment.

As mentioned, fluids and power are supplied to dental handpieces by way of an umbilical cord normally removably connected thereto at a rear end. The connection is usually achieved by an umbilical cord swivel connection which prevents a tangling of the cord. However, this connection normally extends straight in extension of the handpiece, which places a fairly high twisting strain on the wrist of the user, since the straight swivel connection combined with the inherent rigidity of the umbilical cord acts as a sort of lever which exaggerates the actual downward force created by the weight of the cord. This problem has plagued dentists for years with no solution for dental handpieces being available. Various swivel connectors are known in the art for releasable connection of a dental handpiece to the umbilical cord including the working fluid supply and fiberoptic conduits. Examples of swivel connectors are shown in U.S. Pat. Nos. 5,057,015, 6,033,220 and 6,319,003. However, all of these connectors provide only a straight connection between the umbilical cord and the handpiece. Thus, a need exists for a connector which reduces wrist strain.

SUMMARY OF THE INVENTION

It is an object of the present invention to obviate or mitigate at least one disadvantage of existing handpiece designs.

In a first aspect, the present invention provides a turbine design and method of operation, wherein drive air is evenly distributed in an annular chamber extending about the turbine chamber before the air is directed in a generally radial direction onto the turbine wheel. The results are higher torque and self-centering of the turbine, the latter being particularly important for longevity of the bearings used.

In another aspect, the invention provides air bearings for the turbine and the chuck which respectively include a bearing stator of substantially semi-spherical shape and a bearing rotor of complementary shape for fitting into the bearing stator, the bearing rotor being shaped and constructed to fit into the bearing stator with an intermediate air gap for bearing air.

In still another aspect, the invention provides an air bearing arrangement including magnetic portions in the bearing parts for floating the bearings at all times irrespective whether sufficient bearing air is supplied to float the air bearings on the desired air cushion. This provides the advantage that contact of the bearing parts even at low rotational speeds and when the handpiece is shut-off is substantially prevented, thereby reducing bearing wear. Floating the bearing at standstill or in the shut-off condition of the handpiece is also advantageous during sterilization, since the potential for contaminant trapping between respectively contacting bearing parts is substantially reduced.

In a further aspect, the present invention provides a solution to the problem of slippage of the burr in the chuck in high torque situations. A burr/chuck (burr/spindle) combination in accordance with the invention provides a burr with a shaft section of non-circular cross-sectional shape and the chuck or spindle has a protrusion which engages this shaft section to prevent rotation of the burr in the chuck/spindle.

In yet a further aspect of the invention, a burr locking structure is provided which includes a chuck having a central bore for receiving standard burrs, and a socket portion at an outer end of the bore for receiving a lock portion on a burr in accordance with the invention. The socket and lock portion are non-circular in cross-section and of complementary shape to prevent rotation of the lock portion in the socket. This prevents rotation of the chuck relative to the burr and allows for reliable torque transfer. The chuck is preferably constructed to allow visual alignment of the complementary shapes of the socket and lock portion during insertion of the burr.

In still a further aspect of the invention, a burr locking structure is provided which includes a burr having a non-circular shaft end portion for insertion into the chuck/spindle and the latter has a radially inwardly extending protrusion for engagement with the shaft end portion to prevent rotation of the burr relative to the chuck. The protrusion is preferably shaped for automatically aligning the burr with the protrusion upon insertion of the burr.

In still another aspect of the invention, a handpiece construction is provided which addresses the problem of excessive wrist strain by providing an angled swivel connector, which brings the point of attack of the downward force exerted by the weight of the umbilical cord close to the wrist of the user so that twisting strain on the user's wrist (user wrist strain) is significantly reduced.

In a preferred embodiment, the invention provides a medical or dental turbine handpiece including a handle portion for gripping by a user, a drive head connected with the handle portion and forming a turbine housing, a turbine in the turbine housing for rotation about an axis of rotation and having an axial tool bore for receiving a shaft of a rotatable tool insertable into the handpiece, and a pair of axially spaced apart bearings for rotatably supporting the turbine in the turbine housing, characterized in that the handpiece further includes a torque transfer arrangement for transferring torque generated by the turbine to a tool with a shaft portion of non-circular cross-section, the torque transfer arrangement including a locking socket for receiving the shaft portion and having a complementary cross-section for locking the shaft portion against rotation in the socket while permitting axial insertion of the shaft portion into the locking socket, the locking socket being connected to the turbine for rotation therewith.

The locking socket can be separate from the turbine and fastened thereto or integrated into the turbine as an enlarged portion of the tool bore for receiving a tool with a shaft portion in the form of a radially enlarged locking boss having a diameter larger than a diameter of the shaft of the tool.

The locking socket can also be constructed to receive a shaft portion of triangular cross-section, whereby the locking socket has cross-section complementary to that of the shaft portion.

When the locking socket is a part separate from the turbine, the locking socket is preferably a hollow spindle received in the tool bore and fastened therein, the spindle having a cylindrical bore for receiving the shaft portion of the tool and having a torque transfer for locking the shaft portion in the spindle against rotation, while permitting axial insertion of shaft portion into the locking socket. The torque transfer member is preferably a protrusion extending radially inwardly into the cylindrical bore, more preferably a portion of the spindle bent radially inwardly to project into the bore, most preferably a part of the spindle wall stamped radially inwardly to project into the bore. The protrusion where it engages the shaft portion during insertion of the tool into the spindle preferably has a rounded shape for automatically directing the shaft portion past the protrusion to achieve a self-alignment of the shaft portion in the locking socket during insertion of the tool.

The handpiece preferably further includes a tool retaining arrangement for releasably retaining the tool in the tool bore against axial movement after complete insertion of the tool into the bore the burr retaining arrangement including a pair of complementary, interengaging elements respectively incorporated into the spindle and the tool shaft. The retaining arrangement preferably includes a first interengaging element in the form of a resilient tongue incorporated into the spindle and a circular groove in the tool shaft, whereby the resilient tongue and the groove a positioned on the spindle and the tool shaft in such a way that the tongue resiliently engages the groove when the tool is completely inserted into the tool bore.

In another preferred embodiment, the invention provides a torque transfer arrangement for a dental handpiece having a turbine for rotatably driving a burr about an axis of rotation, the burr having a burr shaft with a non-circular shaft portion and the turbine having an axial tool bore for receiving the burr shaft, the torque transfer arrangement, whereby the arrangement includes a locking socket with an axial bore for receiving the shaft portion of the burr shaft, the locking socket being connectable with the turbine for rotation therewith and a torque transfer member connected with the locking socket for locking the shaft portion against rotation relative to the locking socket.

In one variant, the locking socket is preferably insertable into the tool bore. Preferably, the locking socket is a hollow spindle insertable into the tool bore for connection with the turbine and the torque transfer member is a wall portion of the spindle extending radially inwardly into the axial bore. Most preferably, the locking portion of the burr shaft is a terminal portion of the burr shaft and the locking socket is a hollow spindle having a cylindrical bore for receiving the burr shaft, the torque transfer member being a protrusion extending radially inwardly into the cylindrical bore for preventing rotation of the locking portion of the burr shaft in relation to the spindle while permitting axial insertion of the burr shaft into the spindle. To achieve a self-alignment of the terminal portion relative to the protrusion during insertion of the burr, the end surfaces of the protrusion and the terminal portion which come into mutual contact during insertion of the burr shaft into the spindle preferably have a rounded shape for directing the end surface of the terminal portion past the protrusion. To releasably retain the burr in the tool bore, the spindle preferably further includes a burr retaining element extending into the cylindrical bore for releasably engaging a complementary retaining element on the burr shaft to releasably lock the burr shaft in the cylindrical bore against axial movement.

In another variant, the locking socket is incorporated into the turbine and is an enlarged portion of the tool bore for receiving a shaft portion which is a locking boss on the burr shaft having a diameter larger than the diameter of the burr shaft. The locking socket in this variant preferably has a cross-section complementary to a shaft portion of triangular cross-section.

In a further preferred embodiment, the invention provides a medical or dental turbine handpiece for a rotatable tool, having a handle portion for gripping by a user, a drive head connected with the handle portion and forming a turbine housing, a turbine in the turbine housing for rotatably driving the tool about an axis of rotation and having an axial tool bore for receiving the shaft of the tool, a pair of axially spaced apart bearings for rotatably supporting the turbine in the turbine housing, and a pressurized drive air conduit for supplying pressurized turbine drive air to the turbine, whereby the bearings are air bearings, and the handpiece includes a bearing air conduit for supplying pressurized bearing air to the air bearings independent of the turbine drive air. The handpiece preferably further includes a controller for controlling a flow of the pressurized drive air through the drive air conduit separate and independent from a flow of the bearing air through the bearing air conduit.

In yet another preferred embodiment, the invention provides a method of operating a dental handpiece including an air turbine driven by pressurized drive air and a pair of air bearings for supporting the air turbine in the handpiece and operated by pressurized bearing air. The method preferably includes the steps of supplying pressurized bearing air to the air bearings, and supplying pressurized drive air to the turbine independent of the bearing air. The step of supplying bearing air is preferably commenced prior to supplying drive air and continued at least as long as the step of supplying drive air.

In still another preferred embodiment, the invention provides a medical or dental turbine handpiece for a rotatable tool, having a handle portion for gripping by a user, a drive head connected with the handle portion and forming a turbine housing, a turbine in the turbine housing for rotatably driving the tool about an axis of rotation and having an axial tool bore for receiving the tool, and a pressurized turbine drive air supply conduit, whereby the drive head includes a turbine drive air supply chamber connected to the drive air supply conduit for receiving drive air, and the supply chamber extends about the turbine chamber for supplying turbine drive air to the turbine at least at two spaced apart locations distributed about the axis of rotation. The turbine drive air supply chamber is preferably an annular chamber extending concentrically about the axis of rotation. More preferably, the supply chamber supplies drive air to the turbine at a multitude of locations evenly distributed about the axis of rotation. The handpiece can further include a Venturi passage in the drive head connecting the drive air supply chamber to the turbine chamber for accelerating the drive air prior to impinging on the turbine. The Venturi passage preferably includes multiple air guide vanes for directing the turbine drive air onto the turbine in a direction generally radially inwardly towards the axis of rotation.

In a further preferred embodiment, the invention provides a medical or dental turbine handpiece for a rotatable tool having a handle portion for gripping by a user, a drive head connected with the handle portion and forming a turbine housing, a turbine in the turbine housing for rotatably driving the tool about an axis of rotation and having an axial tool bore for receiving a shaft of the tool; and a pair of axially spaced apart bearings for rotatably supporting the turbine in the turbine chamber for rotation about the axis of rotation, whereby the bearings are air bearings. Each air bearing preferably includes a bearing stator having the shape of a spherical section and a bearing rotor of complementary shape. More preferably, the bearing rotor and stator are shaped to define an intermediate bearing gap of even width throughout.

In still a further preferred embodiment, the invention provides a medical or dental turbine handpiece having a handle for gripping by a user, a drive head attached to the handle and forming a turbine chamber, an air driven turbine in the turbine chamber for rotatably driving a tool, the turbine being operated by turbine drive air, and a swivel connector for rotatably connecting the handle to an umbilical cord including at least a supply conduit for the turbine drive air, whereby the swivel connector has an angled connector body for connecting the handle and the umbilical cord at an angle of less than 180 degrees to reduce user wrist strain. The handle and the umbilical cord are preferably connected at an angle between 90 and 180 degrees.

In yet a further preferred embodiment, the invention provides a medical or dental turbine handpiece for a rotatable tool having a shaft including a drive head for rotatably supporting the tool and forming a turbine housing, a turbine in the turbine housing for rotatably driving the tool about an axis of rotation, a pair of axially spaced apart bearings for rotatably supporting the turbine in the turbine housing, a pressurized drive air conduit connected to the turbine housing for supplying pressurized turbine drive air to the turbine, and an exhaust conduit connected to the turbine housing for removing spent turbine drive air from the turbine housing, the handpiece further including a shut-off valve for reducing turbine run down time when the supply of turbine drive air is stopped, the shut-off valve being connected to the drive air conduit and the exhaust air conduit and that the shut-off valve including a closure member normally biased into a closed position wherein the closure member closes both the drive air and exhaust conduits and movable by drive air pressure to an open position wherein the closure member permits passage of drive air and exhaust air through the drive air and exhaust conduits respectively. The bearings are preferably air bearings and handpiece preferably further includes a bearing air supply conduit connected to the drive head for supplying pressurized bearing air to the air bearings, which supply conduit supplies the bearing air independent of the position of the closure member of the shut-off valve. The shut-off valve is preferably incorporated into the handle portion and the closure member is preferably a sleeve axially movable in the handle portion between the open and closed positions.

In yet another preferred embodiment, the invention provides a medical or dental turbine handpiece for a rotatable tool having a working tip, the handpiece including a handle portion for gripping by a users a drive head connected with the handle portion by an intermediate neck portion, the drive head forming a turbine housing, a turbine in the turbine housing for rotatably driving the tool about an axis of rotation and having an axial tool bore for receiving the shaft of the tool, and a pair of axially spaced apart bearings for rotatably supporting the turbine in the turbine housing, the handle portion having a longitudinal central first axis and the neck portion having a longitudinal central second axis, the drive head, neck portion and handle portion being interconnected in such a way that an angle enclosed by the axis of rotation of the tool with the first axis is larger than 90 degrees and with the second axis is less than 90 degrees, and the second axis being oriented at an angle to the first axis such that the tool tip coincides with the first axis.

In still another preferred embodiment, the invention provides a medical or dental turbine handpiece for a rotatable tool, including a handle portion for gripping by a user, a drive head forming a turbine housing, an intermediate neck portion connecting the drive head with the handle portion, a turbine in the turbine housing for rotatably driving the tool about an axis of rotation and having an axial tool bore for receiving the shaft of the tool, and a pair of axially spaced apart bearings for rotatably supporting the turbine in the turbine housing, wherein the handpiece further includes a neck connecting arrangement for releasably connecting the neck portion to the handle portion, the neck connecting arrangement including a socket portion on one of the neck portion and the handle portion and a plug portion on the other of the neck portion and handle portion, and the plug and socket portions being of complementary shape for non-rotatably connecting the neck and handle portions. Preferably, the neck connecting arrangement further includes a snap lock for releasably locking the plug portion in the socket portion.

In another preferred embodiment, the invention provides a dental burr for a dental turbine hand piece, the burr having a working tip and a shaft for insertion into the hand piece, characterized in that the shaft includes a shaft portion of non-circular cross-section for tourque transferring engagement with a burr receiving locking socket in the hand piece. The shaft portion preferably has a cross-section of geometric shape other than circular and preferably triangular. The cross-sectional shape of the shaft portion is preferably symmetrical to the axis of rotation of the burr. If the shaft portion has a cross-sectional shape not symmetrical to the axis of rotation, the cross-sectional shape is preferably complimentary to a cross-sectional shape of the locking socket to prevent rotation of the shaft portion in the locking socket while permitting axial movement of the shaft portion in the locking socket. The burr preferably further has a circumferential retaining groove for releasable engagement with a flexible retaining member in the locking socket when the shaft portion is completely inserted into the locking socket.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the attached Figures, wherein:

FIGS. 1a-c and 2 illustrate the shape and design of a turbine and bearing combination of one embodiment of a handpiece in accordance with the invention;

FIGS. 3a-d show various cross-sections of the drive head of the handpiece of FIG. 2 and illustrating a chuck and burr interlocking structure;

DETAILED DESCRIPTION

Generally, the present invention provides a handpiece for a rotating tool and in particular a medical or dental handpiece and a method of operating and controlling the handpiece. Although for the sake of simplicity reference is made in the following to a dental handpiece, all structural and functional features of the invention are equally applicable to medical handpieces and other handpieces for supporting high speed rotating tools.

Figure 10:
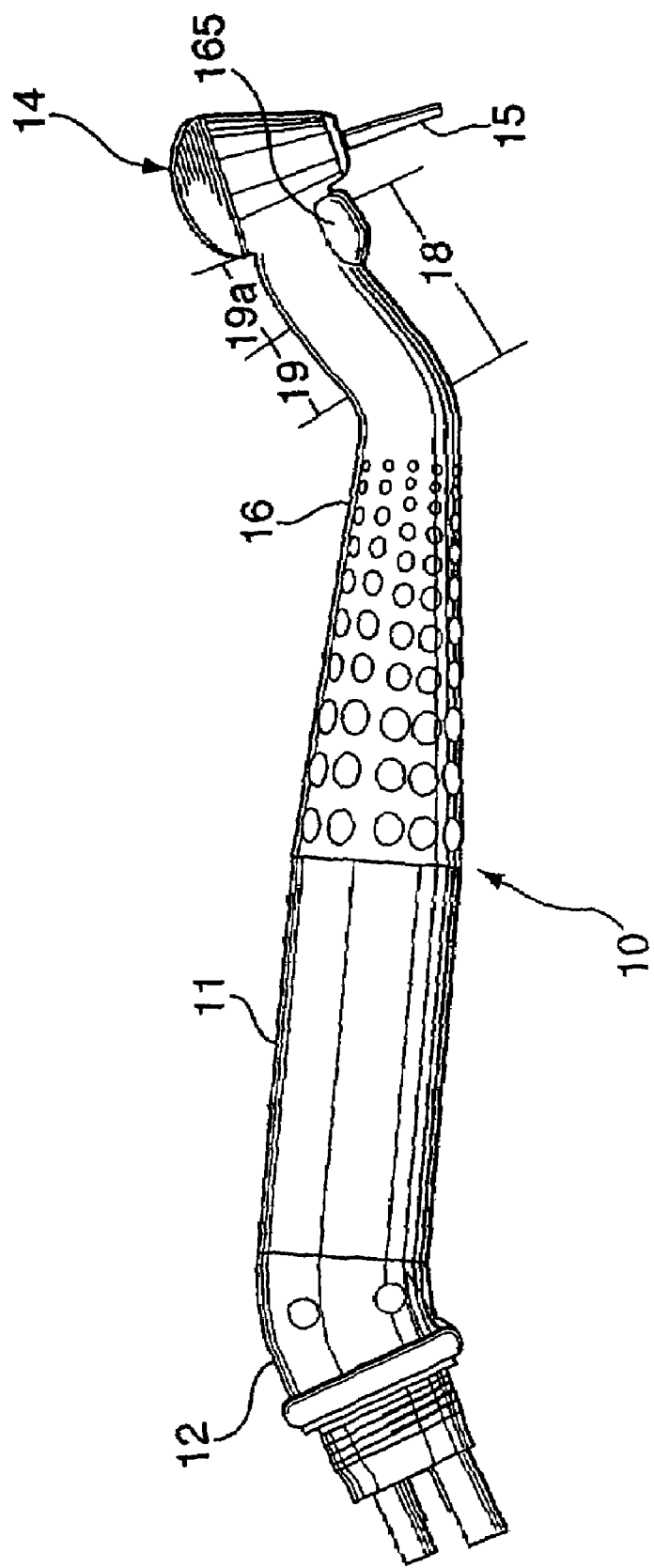
FIG. 10 is a perspective view of one embodiment of a dental handpiece in accordance with the present invention.

As is apparent from FIG. 10, one embodiment of a dental handpiece 10 in accordance with the invention includes a stem/handle portion 11, a plug-in connection 12 for linkage with an umbilical cord 13 (see FIG. 5), and a neck/drive head 16 with a drive head 14 for rotatably supporting and driving a rotatable tool 15. The inventor has identified several construction features of currently sold dental handpieces, which are in need of improvement. The turbine unit, bearing unit, the burr (drill) and chuck interengagement, and the overall ergonomics, construction and connectivity of the handpiece.

Air Bearings

One embodiment of the handpiece 10 of the invention includes an improved drive head 14 with a casing 13 forming a turbine chamber 60 and housing a drive unit 20 consisting of a pair of spaced apart air bearings 30 (see FIGS. 1a-c and 2), a chuck 40 and an air turbine 50 housed in the turbine chamber 60. The bearings 30 are preferably hydrostatic air bearings, but hydrodynamic air bearings can also be used. Each bearing 30 consists of a bearing cup or bearing stator 31 and a bearing body or bearing rotor 32 of complementary shape. The bearing rotor 32 is sized to fit into the stator 31 with sufficient play so that an air gap 33 (bearing gap) of even thickness is created between the bearing parts. The width of the bearing gap 33 is adjusted for optimal operation of the air bearing 30 as will be apparent to the person skilled in the art of air bearings. During use, compressed air is blown into the bearing gap 33 to support the bearing rotor 32 at an even spacing from the stator 31. Numerous styles and types of air bearings are known to the person skilled in the air bearing art and need not be discussed in greater detail herein. The supply of drive air, bearing air and chip air/cooling fluid is controlled such that the bearing air is supplied to the drive head 14 separate from the turbine drive air and irrespective of whether or not the drive unit 20 is rotating. The bearing air supply is preferably controlled by way of a commonly known handpiece stand or cradle (not shown). Preferably, a bearing air supply switch (not illustrated) is incorporated into the cradle, which switches the bearing air supply off when the handpiece is in the cradle and on when it is removed from the cradle. This means the bearing 30 is resting on an air cushion (floated) and ready for operation at all times when the handpiece 10 is lifted off its stand (not shown). This will ensure that the bearing 30 is always active before the turbine 50 is rotated in order to prevent damage to the bearing and to significantly reduce wear. Different implementations of handpiece controllers are known to the person skilled in the art and need not be discussed in further detail herein. Any controller can be used which ensures a constant supply of bearing air (cushioning air) to the bearing 30 when the handpiece is handled, independent of the supply of turbine drive air. The bearing air control can also be accomplished within the handpiece by diverting a constant stream of turbine drive air to the bearings while separately controlling the supply of the turbine drive air to the turbine, as described in more detail with reference to FIGS. 8 and 9.

The bearings are preferably spherical air bearings wherein the bearing rotor 32 and complementary bearing stator 31 parts have a spherically curved surface (in other words the shape of a spherical section) in order to provide a smooth flow of bearing air in the bearing gap 33 and to allow the bearing to support the turbine against axial thrust forces applied by way of the tool 15 (see FIG. 10) as well as thrust forces acting in a direction other than axial, such as those generated upon the application of lateral or oblique loads to the tool tip. This provides a significant advantage over prior art flat pad air bearing arrangements, wherein the air bearing surfaces are substantially flat and extend only in axial or radial direction relative to the axis of rotation of the tool, creating significant turbulence and, thus, air resistance, at the transition between axial and radial bearing surfaces.

Figure 6A:
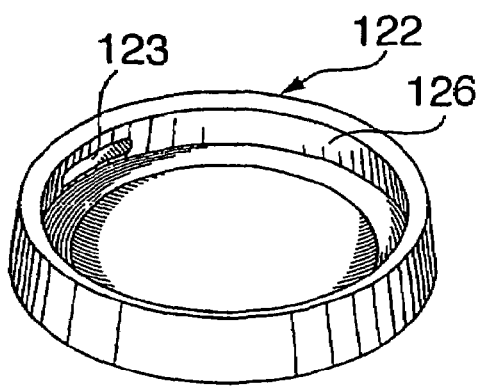
FIGS. 6a-k illustrate the detailed construction of the components of a preferred embodiment of the bearing structure shown in FIGS. 4a-e.
Figure 6B:
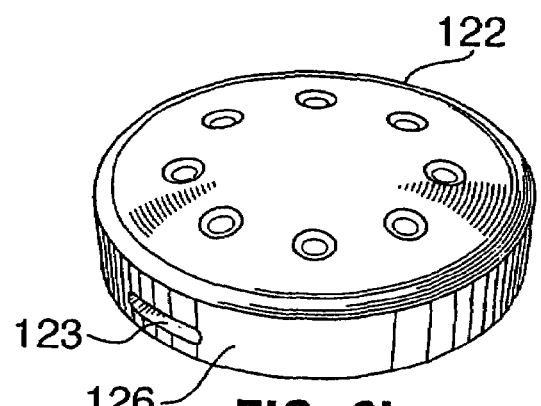
Figure 6C:
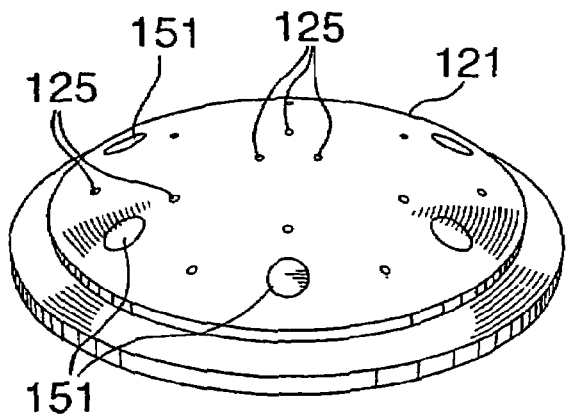
Figure 6D:
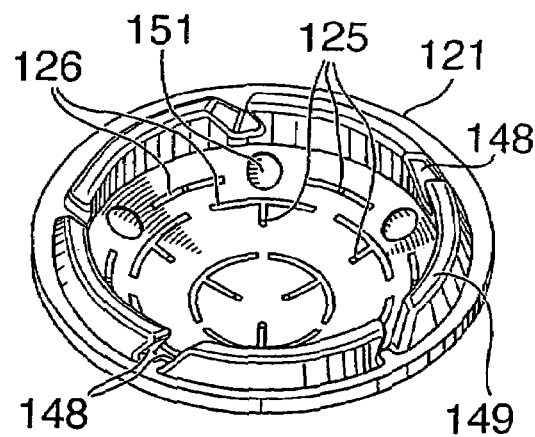
Figure 6E:
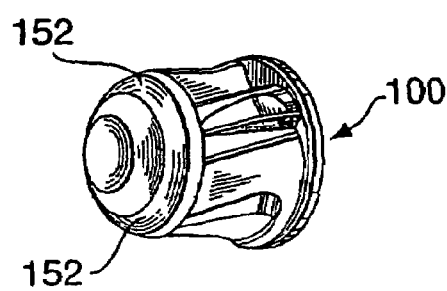
Figure 6F:
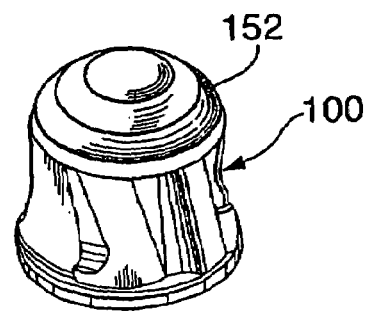
Figure 6G:
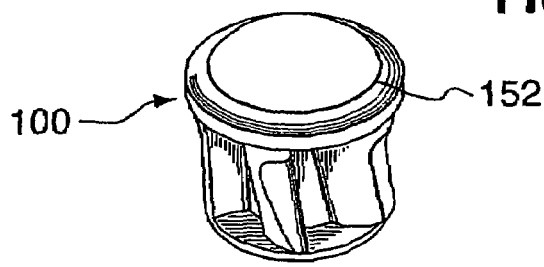
Figure 6H:
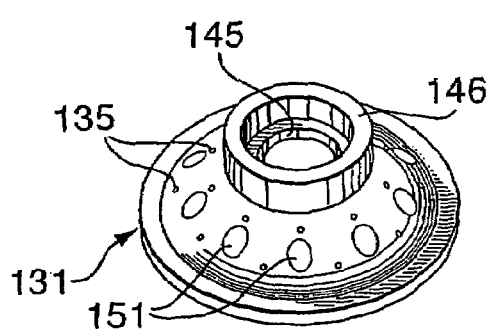
Figure 6I:
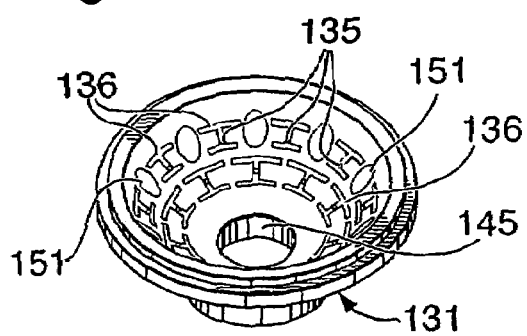
Figure 6J:
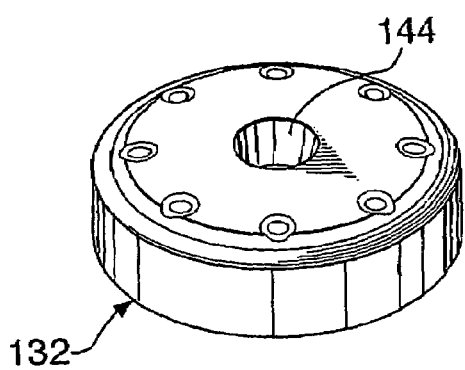
Figure 6K:
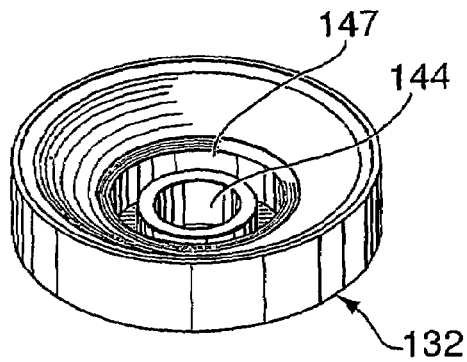

In a preferred embodiment of the handpiece in accordance with the invention as illustrated in FIGS. 4a-d and 6a-l, the turbine impeller wheel and the upper and lower bearing rotors of the upper and lower air bearings 30 are combined into a single turbine rotor unit 100 including an impeller wheel portion 110, a lower bearing rotor portion 130 and an upper bearing rotor portion 120 (see FIGS. 6e-6g). The air bearings 30 are spherical air bearings. Furthermore, the upper and lower bearing stators 121, 131 are respectively associated with an upper and lower casing cap 122, 132, which caps close the top and bottom end of the casing 13 respectively. The respectively opposing bearing surfaces of each bearing rotor and the associated bearing stator are of complementary, even curvature in the shape of a spherical portion. The bearing bodies 120, 130 preferably both have a convexly curved bearing surface and the bearing stators 121, 131 preferably both have a bearing surface of concave curvature. Of course, the curvature of the upper bearing rotor 120 can be concave and that of the lower bearing rotor convex or both can be of the same type of curvature, i.e. concave or convex. Preferably, the bearing surfaces of the top and bottom bearings are however of opposite curvature. Using a pair of spherical bearings with opposite curvature results in a more exact and positive guiding of the parts supported by the bearings. The bearing stators 121, 131 are shaped and sized to sealingly engage the casing 13 about their circumference. This is achieved by way of an annular sealing lip 124 on the upper bearing stator 121 and an annular sealing lip 134 on the lower bearing stator 131, which sealing lips respectively sealingly engage an inner surface of the casing 13. The bearing stators are respectively provided with at least one air passage 125, 135 for bearing air. Preferably, each of the stators is provided with a plurality of air passages 125, 135 (see FIGS. 6c, 6d, 6h, 6i) extending from an outside surface of the stator 121, 131 opposite the associated casing cap 122, 132 through the stator to the inside surface thereof opposite the associated bearing rotor 120, 130. The air passages 125, 135 are preferably evenly distributed over the bearing surface of the stators, but can also be positioned in geometrical arrangements or randomly distributed. The inside surfaces of the bearing stators 121, 131 are respectively provided with at least one recessed air distribution groove 126, 136 for one of the air passages 125, 135. Preferably, the stators are each provided with a plurality of recessed air distribution grooves 126, 136. Each air passage 125, 135 is preferably provided with at least one air distribution groove 126, 136. The grooves 126, 136 are preferably curved along a circular path concentrical with the axis of rotation of the bearing rotors 120, 130. This ensures a more even supply and distribution of bearing air in the bearing gap 33.

The upper casing cap 122 has a circumferential cylindrical sidewall 126 for sealing engagement with the casing 13 and for spacing the cap from the bearing stator 121 to create the upper bearing air chamber 142. The upper casing cap 122, includes an air supply passage 123, for supplying bearing air to the upper bearing stator 121. The bearing air entering through the air supply passage 123 from bearing air supply conduit 140 (see FIGS. 4b, 4d) spreads throughout the upper bearing air chamber 142 and enters the bearing gap 33 through the air passages 125. Spent bearing air exits the bearing gap 33 by flowing around the upper bearing rotor 120 into the turbine chamber 60 and through bearing air drainage openings 148 in an outer rim 149 of the upper stator 121. The lower casing cap 132 and the lower bearing stator 131 respectively have a central burr receiving passage 144, 145. Lower casing cap 132 and lower bearing stator 131 are shaped and constructed to define the annular lower bearing air supply chamber 143. For that purpose, lower bearing stator 131 is provided with a cylindrical spacer wall 146 which is preferably sealingly insertable into a spacer receiving annular groove 147 in the lower casing cap 132. The spacer wall 146 and receiving groove 147 both concentrically surround the burr receiving passage 144 and the axis of rotation of the burr 80 and the turbine wheel 50. The bearing air entering the lower bearing air supply chamber 143 from bearing air supply conduit 140 spreads throughout lower chamber 143, enters the bearing gap 33 through air passages 135, and exits the bearing gap 33 through the burr receiving passage 144. Bearing air is supplied to the casing 13 of drive head 14 separately from the turbine drive air and through a separate air conduit 140 in order to allow the operation of the handpiece as described about wherein bearing air is supplied to the drive head 14 prior to switching on of the turbine drive air, during rotation of the turbine unit 100 and after switching off of the turbine drive air in order to float the turbine unit 100 at all times during rotation. This will be discussed further with reference to FIGS. 8 and 9.

Figure 2:
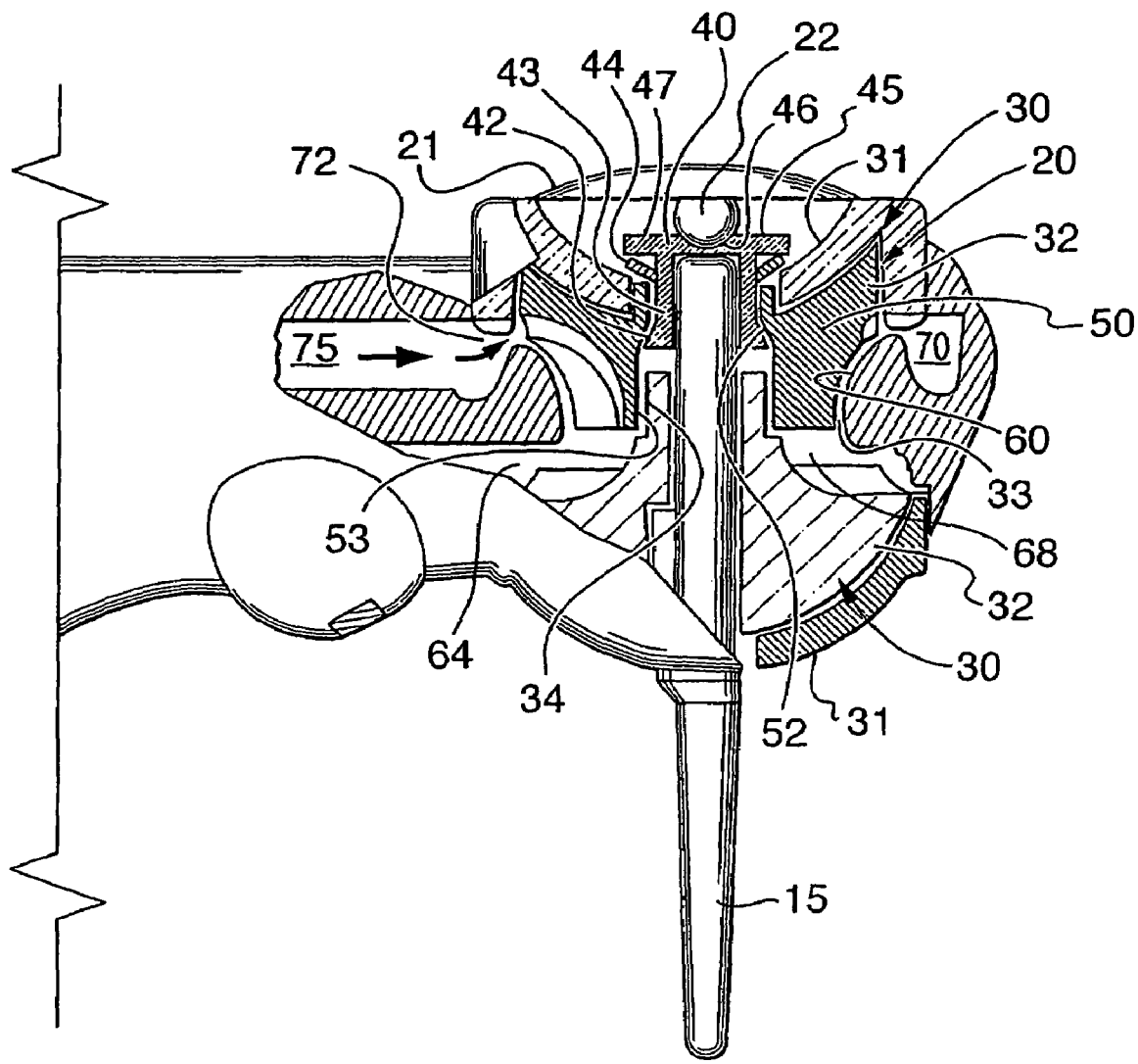
Figure 3C:
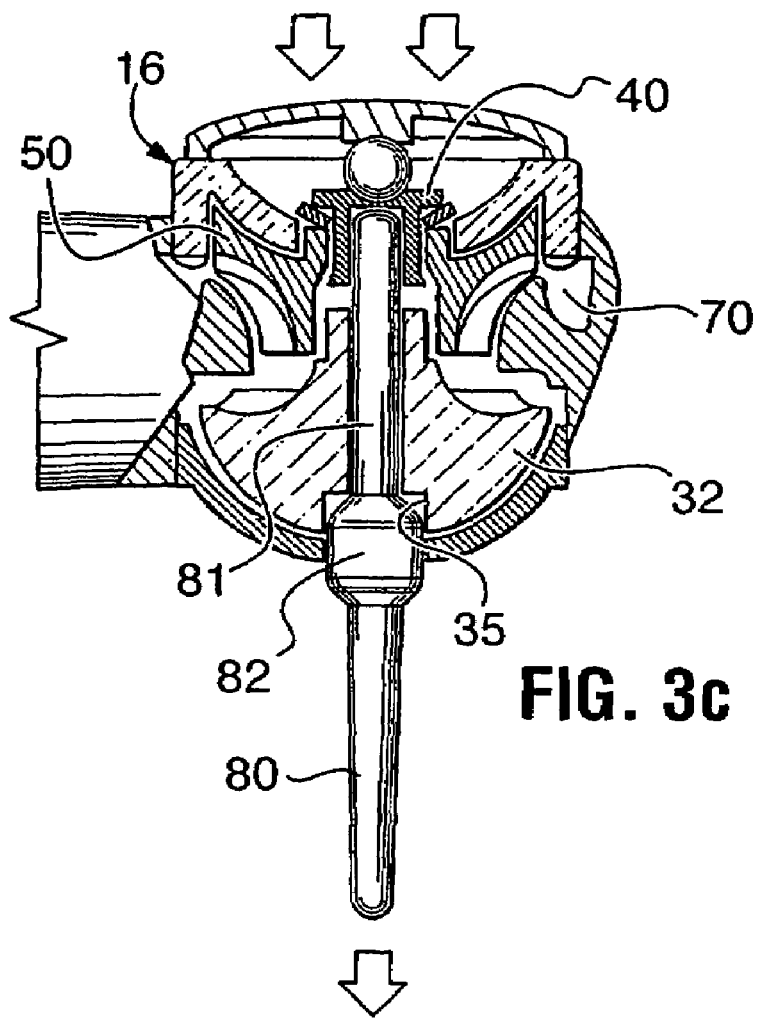
Figure 3D:
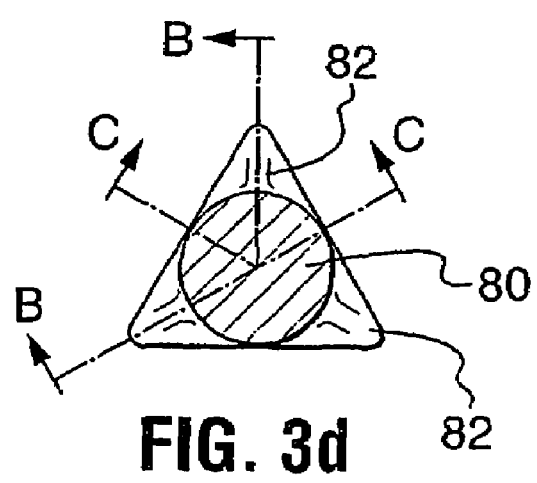
Figure 4A:
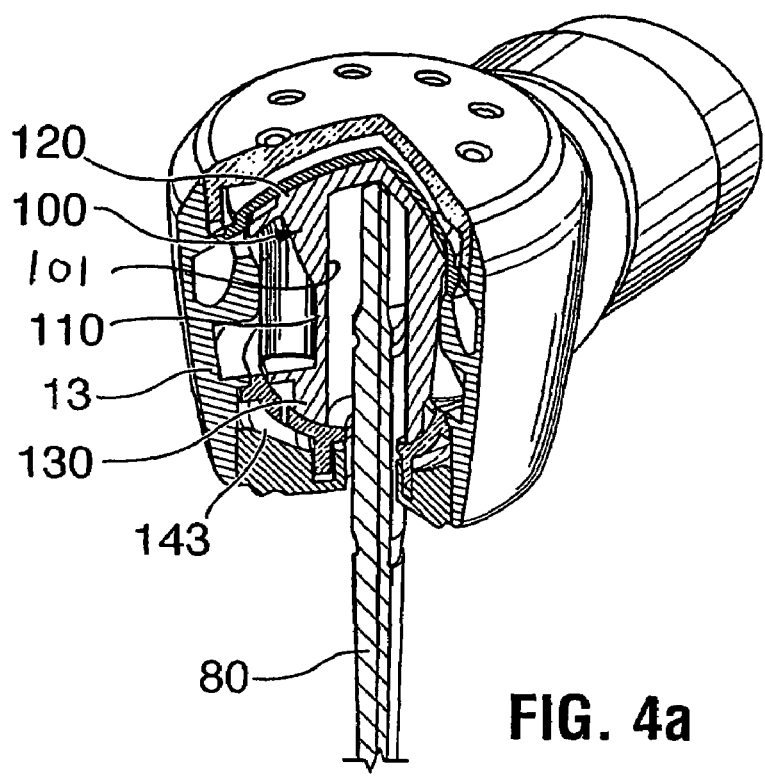
FIGS. 4a-e illustrate the shape and design of another turbine bearing combination in accordance with the invention.
Figure 4B:
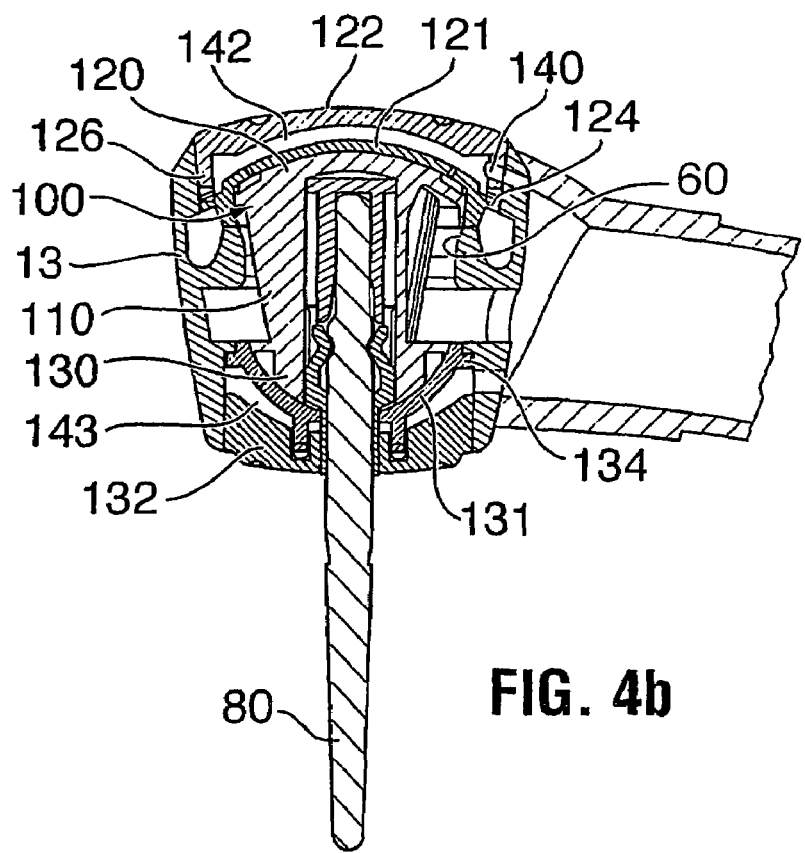
Figure 4C:
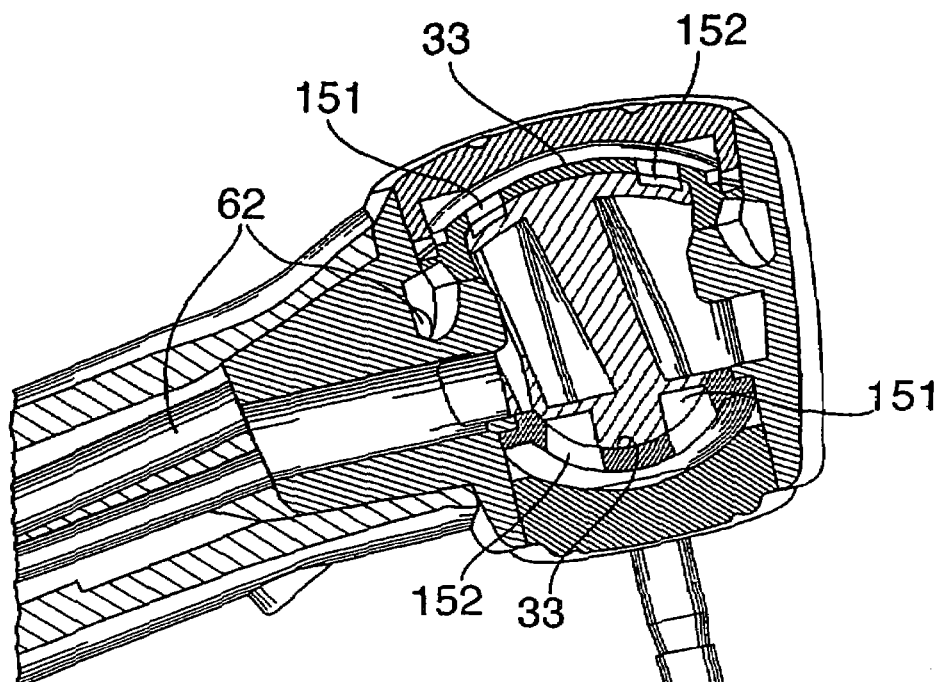
Figure 4D:
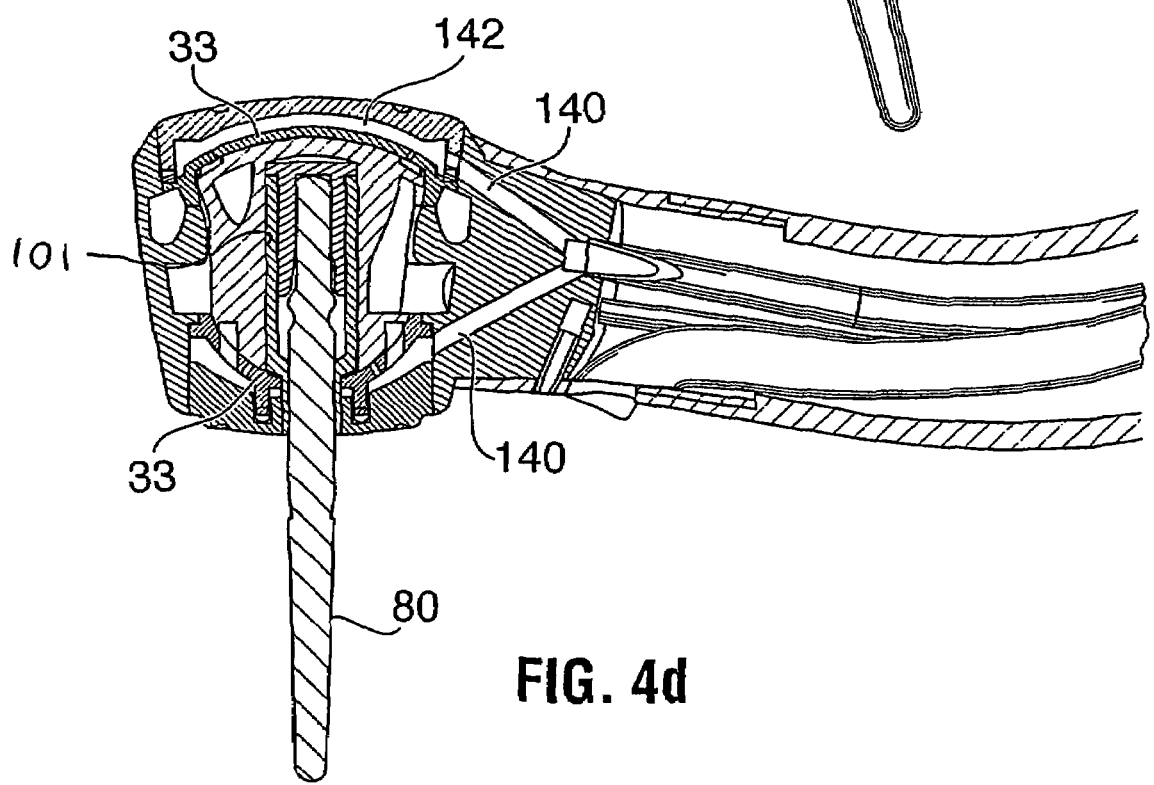
Figure 4E:
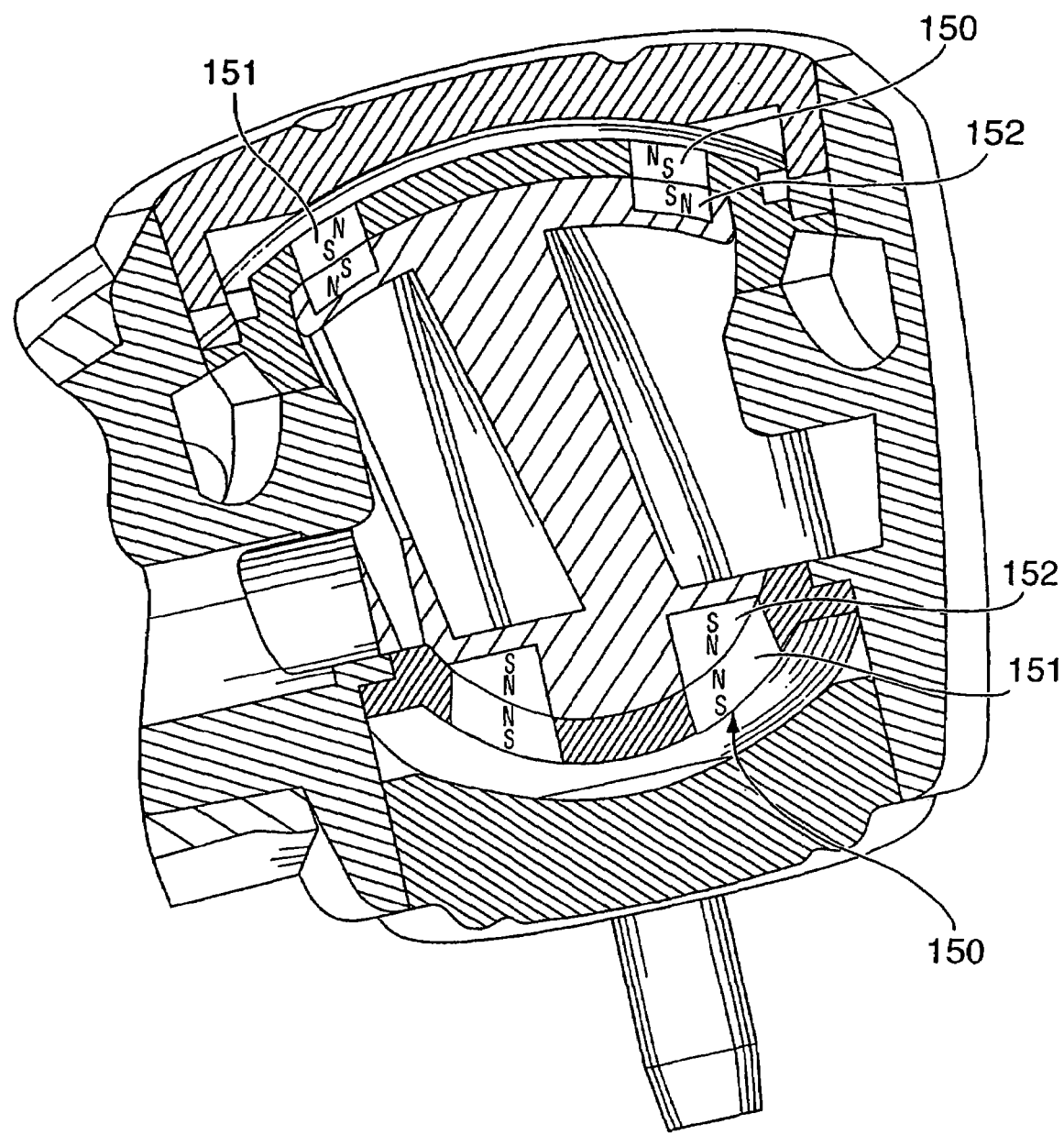

In a preferred embodiment of the air bearing construction illustrated in FIGS. 4a-e and 6a-l, the bearing stators 121, 131 and the upper and lower bearing rotor portions 120, 130 of the turbine unit 100 are provided with a magnetic arrangement for floating the turbine unit 100 in the turbine chamber at all times, independent of any air supply to the handpiece. This means the turbine unit 100 is floated even when the handpiece is not at all connected to the umbilical cord, such as during storage, transport and sterilization of the handpiece or at least the neck/head portion 16 of the handpiece. This reduces damage to the turbine unit and the bearing construction due to vibrations etc. in the shut-off or disconnected condition of the turbine and the handpiece. It further minimizes contact of the turbine unit 100 with the bearing stators 121, 131 during sterilization thereby minimizing the chance of entrapment of contaminants between mutually contacting surfaces and thereby improves sterilization efficiency. The magnetic arrangement includes one or more magnetic inserts 150 (FIG. 4c) in the bearing rotors 120, 130 and bearing stators 121, 131 which inserts are respectively oriented in the bearing parts in such a way in terms of their polarity that magnetic poles of equal polarity are oriented towards one another in each bearing rotor/bearing stator combination. Since magnetic poles of equal polarity repel each other, the magnetic inserts 150 result in the turbine unit 100 being forced away from both bearing stators 121, 131 and, thus, kept afloat therebetween. The magnetic inserts 150 are preferably in the form of cylindrical magnet discs 151 embedded into the bearing stators 121, 131 and an annular magnet ring 152 embedded into each of the bearing rotors 120, 130. The magnetic discs 151 are preferably evenly spaced from one another and aligned along a circle concentrical with the axis of rotation of the turbine unit 100, which circle preferably has a radius equal to the mean radius of the annular magnet ring 152 so that the magnetic discs 151 are preferably positioned over the center line of the magnet ring 152 for the achievement of a maximum repelling force. As mentioned, the polarity of the respectively opposing magnet discs and magnet ring is selected such that the respectively opposing surfaces thereof are of equal polarity and repel each other. One possible polar orientation of the magnetic inserts 150 is shown in FIG. 4e, which is an enlarged view of the drive head shown in FIG. 4c. Of course the exactly opposite orientation for each insert 150 is also possible. The respective polar orientation of the two magnetic rings 152 on the upper and lower bearing bodies 120, 130 is selected such that the mutually opposing poles are of opposite polarity. This provides that the magnetic rings 152 will be attracted to each other, reducing the potential for the magnetic rings 152 being forced out of the associated bearing rotor. Furthermore, arranging the polarization of the magnetic rings in this way potentially results in an overlapping and reinforcing of their respective magnetic fields rather than an attenuation thereof.

The turbine unit 100 and bearing stators 121, 131 are preferably made of metallic materials well known to the person skilled in the art. The magnetic inserts 150 are preferably commercially available permanent magnets inserted into receiving pockets in the bearing stators 121, 131 and bearing rotors 120, 130 and fastened therein, preferably with adhesive. The running surfaces of the bearing stators and bearing rotors are preferably polished to provide the best possible bearing air cushion. The magnetic inserts are preferably inserted into the bearing stators and rotors before the polishing operation to prevent any bearing surface unevenness. This will be apparent to the person of skill in the art of air bearings. The running surfaces may also be anodized to provide a smoother bearing surface.

Radial Air Flow Turbine

The drive unit 20 of a handpiece in accordance with the invention as shown in FIGS. 1-3e generally includes the air turbine wheel 50 and the dental tool (burr) receiving chuck 40 which are supported in the handpiece drive head 14 by the bearings 30. Air turbine impeller wheel 50 is connected with the bearing rotor 32 of the lower bearing 30 for torque transfer. It will be readily apparent to the person skilled in the art that this connection can be achieved in a multitude of ways, all of which are usable within the context of the present invention as long as the connection is co-axial and prevents rotation of the turbine relative to the bearing rotor. Examples of applicable types of connection are an adhesive connection, an interlocking connection (lock and key type) between the two parts, a meshing connection of complementary non-circular parts, a press-fitting of the bearing rotor 32 and the turbine wheel 50, etc. The bearing rotor 32 of the lower bearing 30 can also be made unitary with the air turbine wheel 50 as a single turbine body of unitary construction, such as the turbine body of the embodiment of FIGS. 6e-6g. In one preferred embodiment as illustrated in FIGS. 3a-c the bearing rotor 32 includes an axially protruding connection flange 34 which is received in an axial bore 53 in the turbine wheel 50. The flange 34 and bore 53 preferably include respectively complementary and preferably meshing, axially extending radial protrusions 55 in this embodiment which allow axial insertion of the flange 34 into the bore 53, while preventing rotation of the flange in the recess. The improved drive unit of the invention includes a radial airflow turbine in contrast to the paddle wheel type turbine commonly known. The radial air flow turbine design requires that the drive air be supplied to the turbine radially inwardly rather than tangentially. This is achieved in the illustrated embodiment in accordance with the invention by providing an annular drive air supply chamber 70 in the casing 13 which chamber 70 extends concentrically about the axis of rotation of the turbine. Radially inwardly, the air supply chamber 70 is connected with the turbine chamber 60 through a Venturi passage 72 (see also FIGS. 1a, 1c). The Venturi passage 72 preferably extends continuously about the axis of rotation and provides a restriction or nozzle for speeding up the drive air supplied into the turbine chamber 60 from the air supply chamber 70. The latter is supplied with pressurized drive air by a drive air supply conduit 75 extending through the handpiece and the umbilical cord. The drive air is evenly distributed in the annular air supply chamber 70 and redirected radially inwardly towards the axis of the turbine wheel 50 by a plurality of stationary radial air vanes 74 positioned in the Venturi passage 72. Directing the drive air radially inwardly significantly reduces parasitic airflow (drag) compared to paddle wheel type turbines in which the drive air is supplied tangentially at the circumference of the turbine 50. Radial drive air supply also generates additional torque due to the extended engagement time of the air with the turbine 50 and the simultaneous engagement of drive air with all turbine vanes rather than only one as with tangential flow constructions. The torque output of the turbine 50 is also improved by using the annular Venturi air supply nozzle 72, since it causes the drive air to speed up immediately prior to impact with the turbine 50. The Venturi passage 72 further creates a back pressure in the annular chamber 70. This equalizes drive air pressure throughout the air supply chamber 70, which then results in an even drive air pressure about the whole circumference of the turbine 50. Supplying the drive air radially and evenly about the circumference of the turbine also overcomes the significant problem of asymmetrical loading of the turbine bearings in prior art designs with tangential drive air supply. The evenly distributed drive air of the handpiece of the present invention provides an automatic centering of the turbine wheel 50, greatly reducing radial stress on the bearings 30, especially the top bearing. The turbine blades 54 in axial cross-section are convexly curved in direction of rotation to deflect radially impinging drive air against the direction of rotation of the turbine wheel. The turbine blades are preferably also inclined in axial direction of the wheel and in terms of drive air flow in a direction away from the direction of rotation to generate additional torque. Pressurized turbine drive air is supplied to the drive head 14 by a drive air supply conduit 62 (see FIG. 4c) which is connected to the annular air supply chamber 70 and extends through the handpiece and the umbilical cord to a pressurized air source (not shown) well known to the person skilled in the art. Drive air entering the turbine chamber 60 through Venturi passage 72 impinges on all turbine wheel blades 54, flows radially inward along the blades towards the core of the turbine wheel 50 and axially downward along the blades 54, to collect in an annular drive air exhaust chamber 68 and exit through air exhaust conduit 64.

Chuck and Burr Lock

The embodiment of the handpiece 10 of the invention illustrated in FIGS. 3a-3e incorporates a torque transfer arrangement for transferring torque generated by the turbine to a tool with a shaft portion of non-circular cross-section, the torque transfer arrangement including a locking socket for receiving the shaft portion and having a complementary cross-section for locking the shaft portion against rotation in the socket while permitting axial insertion of the shaft portion into the locking socket. The locking socket is connected to the turbine for rotation therewith. This torque transfer structure transfers torque generated by the turbine wheel 50 to the burr 80 by preventing slipping of the burr 80 in the tool receiving bore of the turbine, a problem common with prior art handpieces.

The torque transfer structure generally includes a torque transfer shaft portion of non-circular cross-section on a shaft of the burr 80 and a locking socket 35 non-rotatably connected with the turbine and having a shape complementary to the shaft portion to prevent rotation of the shaft portion in the socket and, thus, relative to the turbine. The locking socket can be separate from the turbine and connected thereto through an intermediate part, such as the bearing rotor 32, or can be directly connected with the turbine.

In a preferred embodiment as illustrated in FIGS. 3a-d, the torque transfer structure includes the chuck 40, the bearing rotor 32 and a locking socket 35 integrated in the bearing rotor 32 of the lower bearing. The burr 80 is received in an axial tool passage extending through the bearing rotor 32, the chuck 40 and the turbine wheel 50. The burr 80 and chuck 40 are designed so that the burr is held in the chuck by friction. This is achieved by forcing the chuck 40 against the burr 80. Chuck 40 includes a ramped shoulder 42 extending about the outer circumference of the chuck 40 at a bottom end 43 thereof. The turbine wheel 50 includes a correspondingly ramped seat 52 in the bore 53. Chuck 40 is axially movable in the bore 53 between a locking position wherein the shoulder 42 engages seat 52 and the bottom end 42 of the chuck 40 is forced radially inwardly, and a release position wherein the shoulder 42 is axially spaced from the seat 52 and a burr 80 is freely insertable or removable from the chuck 40. Of course, chuck 40 is made of a material which provides the requisite amount of flexibility to allow for sufficient deformation of the chuck 40 to frictionally grip an inserted burr 80. Chuck 40 is normally urged into the locking position by a Belleville washer 44 extending about the chuck 40 below a radial top flange 45 and forcing the top flange 45 away from the turbine wheel 50. A flexible push button actuator 21 allows the operator to move the chuck 40 into the release position by way of an intermediate actuator ball 22 received in a complementary seat 46 in the top end 47 of the chuck 40. Depressing the push button 21 forces ball 22 and chuck 40 downward until shoulder 42 no longer engages seat 52. This type of frictional burr locking and chuck release arrangement is standard in the art and need not be further described in detail.

Rotation of the burr 80 relative to the chuck 40 and turbine 50 is prevented by an interlocking or intermeshing structure including complementary portions such as lock and key type portions on the bearing rotor 32 and the burr 80 respectively. The burr 80 has a shaft 81 of generally constant cross-section for insertion into the burr receiving tool bore of the bearing rotor 32, the chuck 40 and the turbine wheel 50. The shaft includes an enlarged locking boss 82 of non-circular cross-section. The bearing rotor 32 of the lower bearing 30 includes a locking socket 35 complementary in shape to the locking boss 82 of the shaft 81. The socket 35 fittingly receives the locking boss 82 so that rotation of the burr 80 relative to the bearing rotor 32 and thereby the turbine 50 is thereby reliably prevented. The axial position of the boss 82 on the shaft is selected such that the boss 82 non-rotatably engages the socket 35 when the burr 80 is fully inserted into the chuck 40. Thus, the problem of burr slippage at high torque commonly observed in prior art handpiece constructions is thereby overcome. The boss 82 and socket 35 can have any cross-sectional shape other than circular, as long as their respective shapes reliably prevent rotation of the burr 80 relative to the socket 35 when the burr 80 is fully inserted into chuck 40. The socket 35 is preferably positioned on the bearing rotor 32 to be easily visible to the user. This allows the user to visually align the shape of the boss 82 with the shape of the socket 52, thereby facilitating insertion of the burr 80.

In another preferred embodiment, as illustrated in FIGS. 4a-d and 5a-b, the locking socket 200 is constructed as a two piece spindle including a torque lock 210 and an alignment sleeve 220. The alignment sleeve 220 is sized and shaped for insertion into a central tool bore 170 of the turbine unit 100. This alignment sleeve 220 and the torque lock 210 can also be made in a single piece. Thus, this torque transfer arrangement for a dental handpiece 10 with a turbine unit 100 for rotatably driving a burr 80 about an axis of rotation, the burr 80 having a burr shaft 81 with a non-circular shaft portion 83 (see FIG. 5a) and the turbine having an axial tool bore for receiving the burr shaft 81 includes a locking socket 200 with an axial bore 221 for receiving the shaft portion 83 of the burr shaft 81, the locking socket 200 being connectable with the turbine for rotation therewith and a torque transfer member 210 connected with the locking socket 200 for locking the shaft portion 83 against rotation relative to the locking socket 200. In the preferred embodiment of FIGS. 5a and b, the locking socket 200 is a two piece socket including a hollow spindle 220 and the torque lock 210. The locking socket 200 is connected to the turbine for rotation therewith. This is achieved by adhesive or friction connection of the torque lock 210 with the spindle 220 and connection of the latter with the turbine unit 100 (see FIGS. 4a-d). The spindle 220 can be non-rotatably connected to the turbine unit 100 for reliable torque transmission by compression fitting the spindle 220 into the turbine, but is preferably adhesively connected thereto. Thus, the locking socket 200 is insertable into the tool bore 101 of the turbine unit 100 and connected with the turbine. The locking socket 200 includes the hollow spindle 220 insertable into the tool bore 101 for connection with the turbine and a torque transfer member 230 incorporated in the torque lock 210 and extending radially inwardly into the axial bore 221 of the spindle 220. Although the torque lock 210 and the spindle 220 are shown in the illustrated embodiment as separate parts, they function as a single part, once interconnected, preferably by adhesive bonding, together forming a burr receiving spindle. However, they can also be made as a single part in the form of a spindle 220 fittingly receiving the burr shaft 81 and having an inwardly extending torque transfer member 230 directly incorporated into the spindle 220. The torque transfer member 230 is a protrusion extending radially inwardly into the cylindrical bore 221 of the spindle 220 for preventing rotation of the locking portion 83 of the burr shaft 81 in relation to the spindle 220, while permitting axial insertion of the burr shaft 81 into the spindle 220. Thus, the torque lock 210 has at least a portion of non-circular cross-section. That is, the portion including the torque transfer member 230, which renders the cross-section non-circular and non-complementary to the non-circular shaft portion 83. The torque transfer member 230 is adapted for engaging and locking at least a portion of the non-circular shaft portion 83 to prevent rotation of the burr shaft 81 relative to the torque lock 210. The spindle 220 and torque lock 210 are preferably made of metal and the torque transfer member 230 is preferably stamped from the torque lock 210 or the spindle 220. As will be apparent from FIG. 5a, the ends of the torque transfer member 230 and the locking portion 83 of the burr shaft 81 which come into mutual contact during insertion of the burr shaft 81 into the spindle 220 have a rounded shape for directing the end surface of the locking portion 83 automatically past the torque transfer member 230 to achieve a self-alignment of the locking portion 83 relative to the torque transfer member 230 during insertion of the burr 80.

The construction of the locking socket 200 as a spindle 220 also allows the use of the locking socket in conventional drive head arrangements including a turbine wheel and a pair of mechanical bearings such as ball bearings. The spindle 220 can be used for coaxial alignment of the bearings and the turbine and, when rigidly connected to the turbine (for example through adhesive bonding) for reliable torque transfer from the turbine to the burr. Thus, conventional handpieces subject to the problem of burr slipping at high torque can be retrofitted with a torque transfer arrangement in accordance with the invention.

Figure 5A:
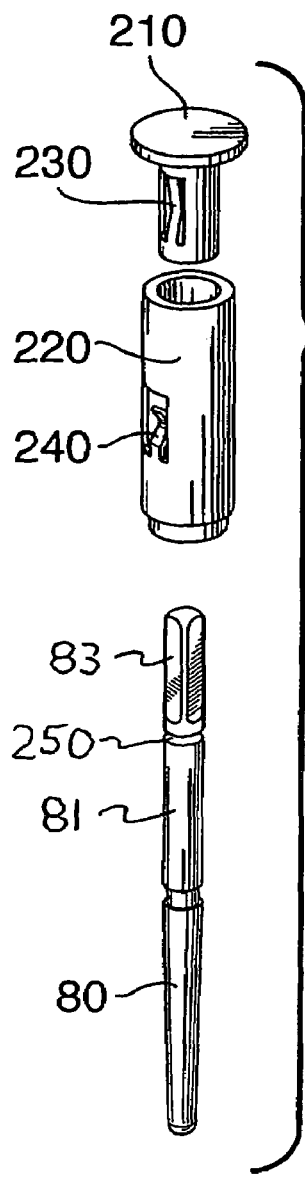
FIGS. 5a-b show another burr locking structure in accordance with the invention as included in the embodiment shown in FIGS. 4a-e.
Figure 5B:
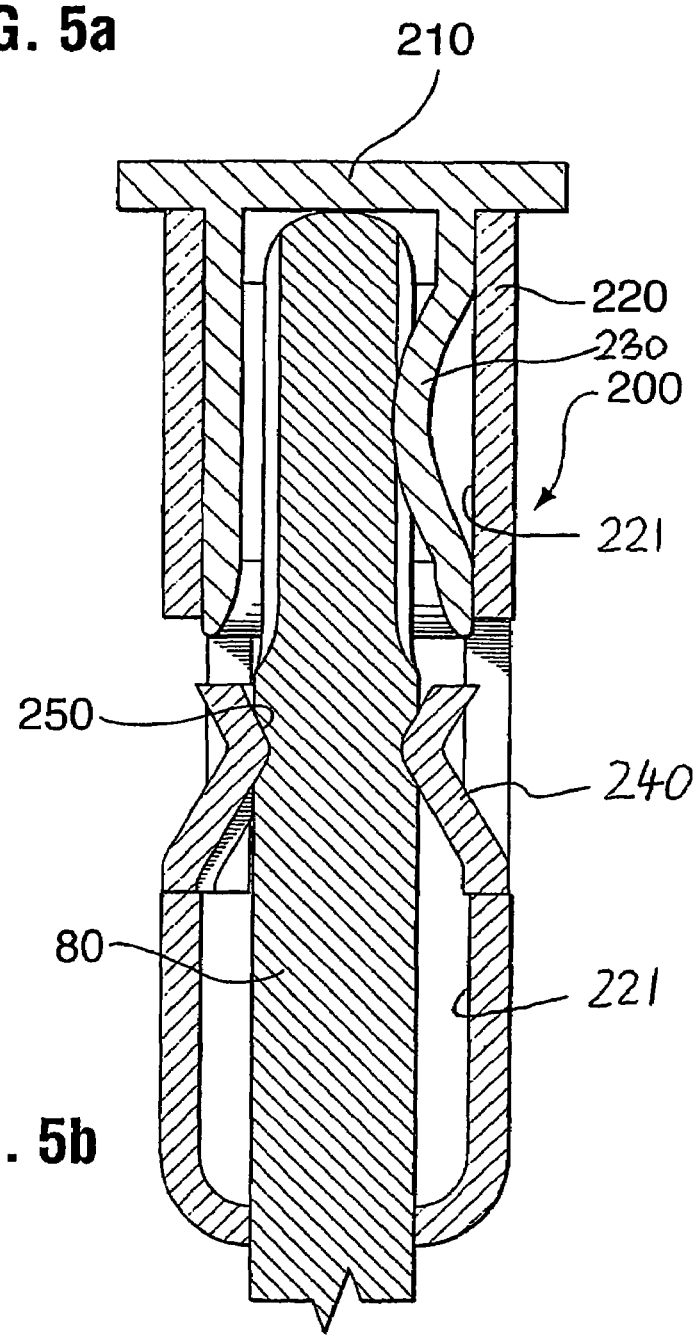

The torque transfer arrangement of the embodiment shown in FIGS. 5a and b also includes a burr retaining element 240 of the spindle 220 extending into the cylindrical bore 221 for releasably engaging a complementary retaining element 85 on the burr shaft 81 in the form of a circular groove, to releasably lock the burr shaft 81 in the cylindrical bore 221 against axial movement. The retaining element or tab 240 is also preferably made by stamping a portion of the wall of the spindle 220 radially inwardly. The tab 240 preferably has sufficient flexibility and durability to allow repeated burr insertions and removals. The tab 240 is also preferably sufficiently strong to provide a distinct snap-in feeling to the user inserting the burr 80, when the tab snaps into the burr groove 85.

Drive Head Quick Connect

Figure 7A:
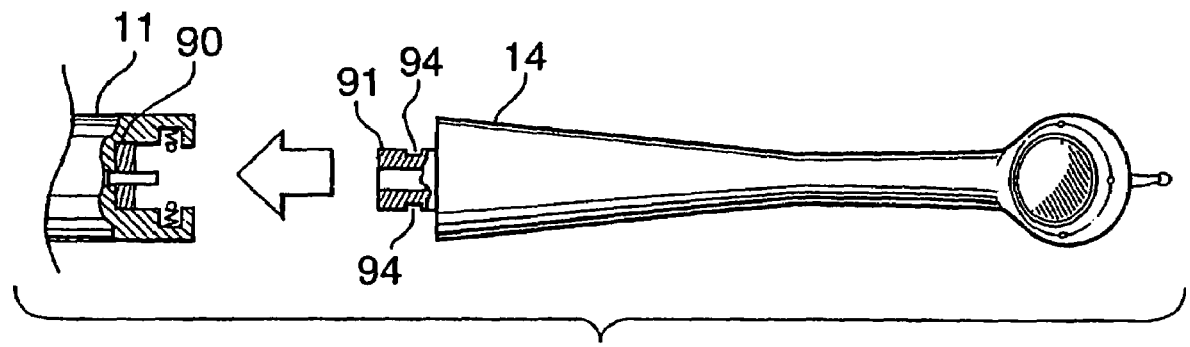
FIGS. 7a-c show perspective, partially cut-away and cross-sectional views of the handle (stem) and neck portion quick coupling in accordance with the invention, FIG. 7c showing a cross-section through the quick coupling taken along line A-A in FIG. 7b.
Figure 7B:
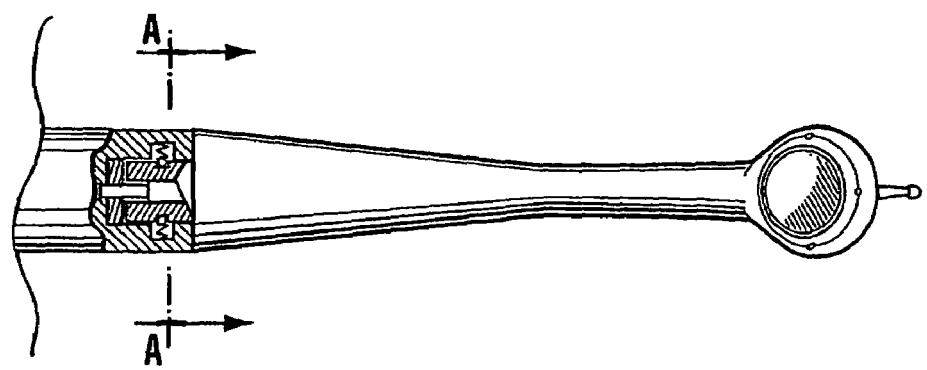
Figure 7C:
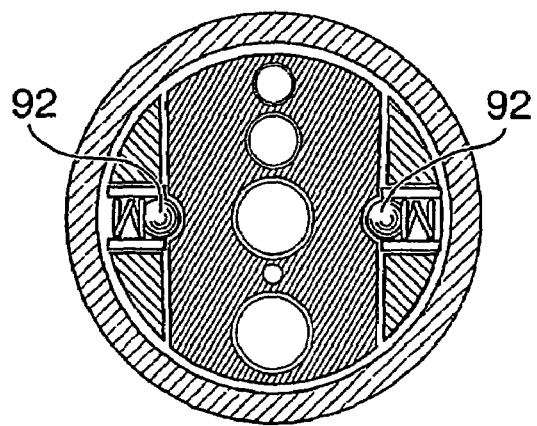

Conventional handpieces include a neck/drive head which houses the drive unit and a stem/handle portion for manipulation by the dentist, which stem portion includes at the rear end a coupling for the umbilical cord housing the air and water supply lines. The neck and stem portions are generally combined in a single part. This is disadvantageous since the coupling will be subjected to harsh sterilization conditions when the handpiece is sterilized, which often leads to premature failure of the coupling components (such as O-rings). The preferred embodiment of the handpiece of the present invention as illustrated in partially cut-away view in FIG. 4 is constructed in two parts so that the neck/drive head 14 can be separated from the handle/stem portion 11 and separately sterilized. According to existing health standards, the handle portion need not necessarily be heat sterilized. Thus, with the handpiece construction of the present invention, the drive head can be heat sterilized and the handle portion can be sterilized by another method less detrimental to the sensitive components of the umbilical cord connection 12 (see FIG. 7). A quick connect coupling is provided between the two parts which is non-rotatable and includes a connector socket 90 inserted into the handle sleeve 17 and a complementary connector plug 91 integral with the neck portion 14. Socket 90 and plug 91 are of complementary shape so that the plug 91 non-rotatably fits into the socket. The connection is constructed as a snap-fit connection by way of a pair of spring loaded pins or balls 93 in the connector socket 90 which respectively engage one of a pair of snap-in recess 94 in the plug 91, when the plug is fully inserted in the socket.

Turbine Auto-Stop

Figure 8:
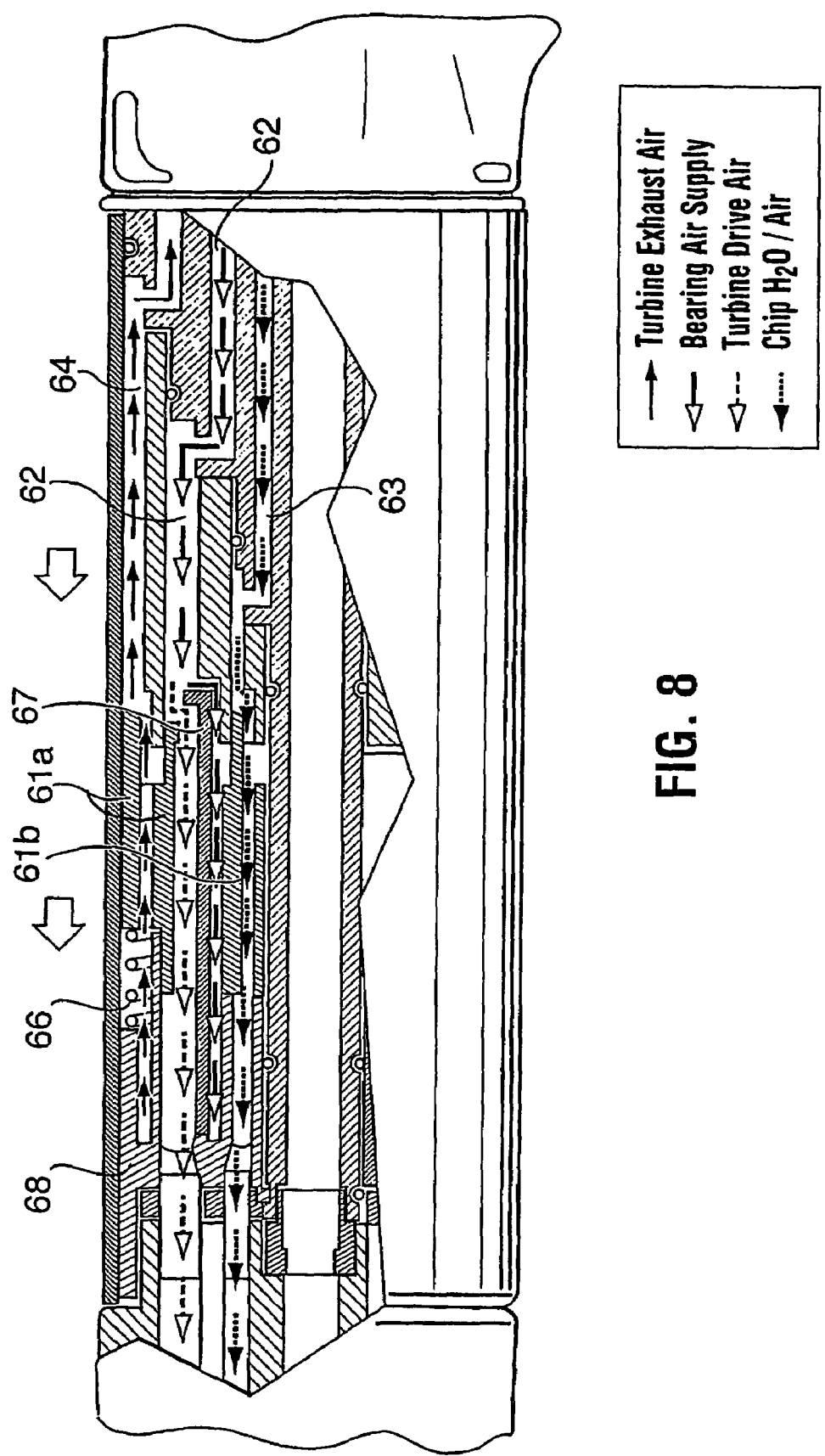
FIG. 8 illustrates the auto-shutoff mechanism in accordance with one embodiment of the invention.
Figure 9:
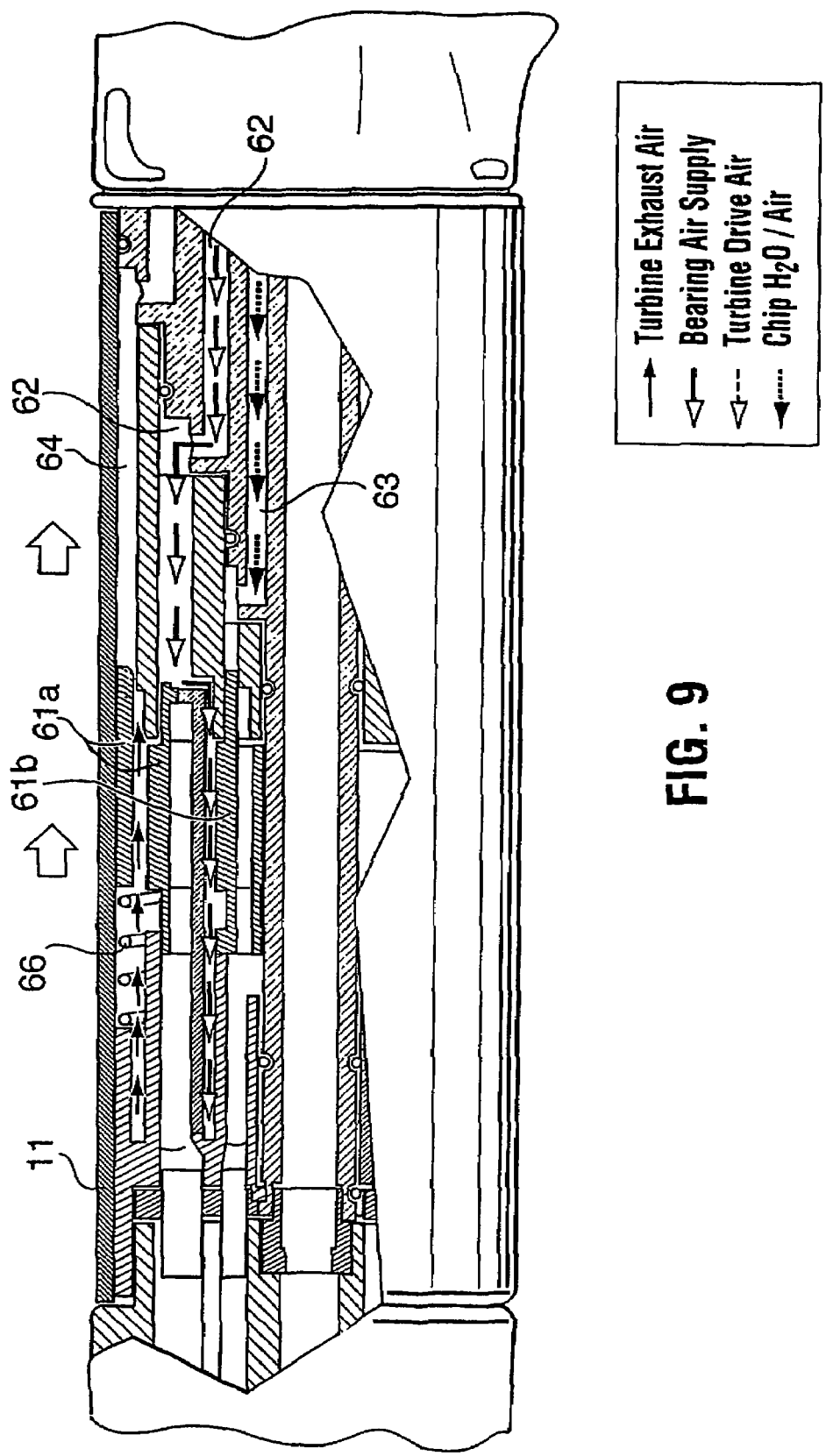
FIG. 9 illustrates the auto-shutoff mechanism of FIG. 8 in a different operational state.
Figure 14:
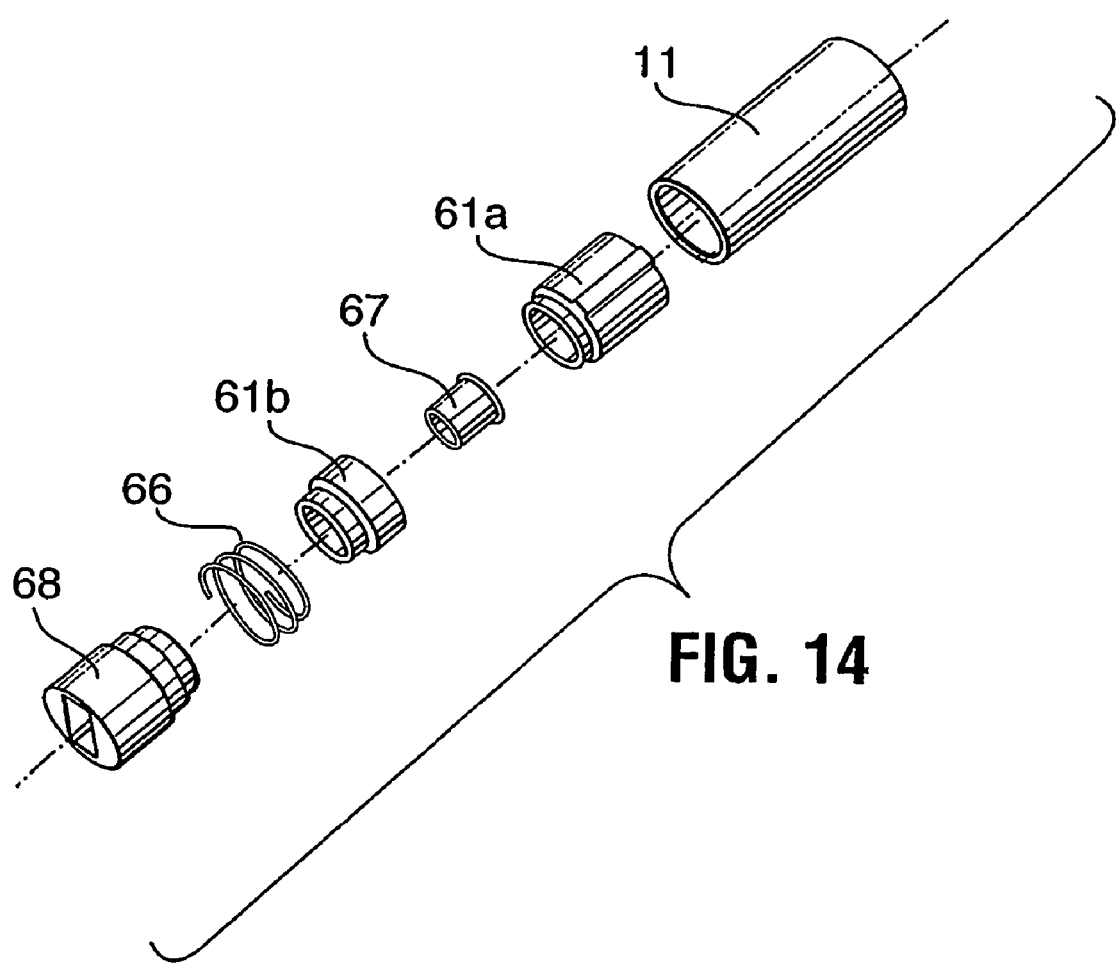
FIG. 14 is an exploded view of the handle portion as shown in FIGS. 8 and 9.

The handpiece is further provided with an automatic shut-off valve for the turbine drive air and the turbine exhaust air and, preferably, also the chip water/air mixture. This provides for instant on/off of the turbine and chip water/air. That is a very important advantage, since with current handpiece designs the dentist must wait until the burr has slowed to a stop before removing the burr from the patient's mouth in order to avoid injury to the patient's tongue or lips. The automatic shut-off valve as shown in FIGS. 8 and 9 includes a closure member, in this case a pair of cooperating valve sleeves 61a, 61b operated by the turbine drive air (see FIGS. 8, 9 and 14). The valve sleeves 61a, 61b are normally biased by a spring 66 into the closed position as shown in FIG. 8, wherein they close the drive air supply conduit 62, the turbine air exhaust conduit 64, and preferably also the chip water/air supply conduit 63. Thus, in the closed position of the valve sleeves 61a 61b, no air can be supplied to and or exhausted from the turbine chamber 60, which quickly slows down the turbine 50 due to turbulence in the air entrapped in the turbine chamber. A quick stopping of the turbine prevents the build up of a vacuum in the turbine chamber 60 during rundown of the turbine 50 and, thus, prevents the drawing of contaminants into the turbine chamber during rundown. When turbine drive air is supplied to the handpiece through operation of a handpiece controller/rheostat known in the art (not shown; usually a foot pedal) the valve sleeves 61a, 61b are moved by the drive air pressure against the force of the spring 66 from the closed position shown in FIG. 8 to the open position shown in FIG. 9. In the open position, the valve sleeves 61a, 61b do not obstruct the turbine drive air supply conduit 62, the turbine air exhaust conduit 64 and the chip water/air supply conduit 63. As soon as the drive air supply is stopped, the biasing spring 66 moves the valve sleeves 61a, 61b back to the closed position in which they again block the turbine drive air supply conduit 62, the turbine air exhaust conduit 64 and the chip water/air supply conduit 63. This completely entraps the air found in the turbine chamber 60. As a result no vacuum can be created in the turbine chamber 60 and the turbine comes to a substantially instantaneous stop due to turbulence created in the chamber. It is important to note that the valve sleeves 61a, 61b are preferably constructed to not affect the supply of bearing air if an air bearing is used. Bearing air is split off the drive air supply prior to engagement of the drive air supply with the valve sleeve by a cylindrical air flow splitter 67. This ensures continuous operation readiness for the air bearing, irrespective of the operational state of the turbine, which prevents damage to the air bearing caused by lack of bearing air supply during rundown of the turbine. In the preferred method of operating a handpiece in accordance with the present invention, the bearing air supply activation is coupled with the handpiece cradle (not shown) in such a way that bearing air is supplied to the handpiece for the whole time the handpiece is off the cradle.

Neck Portion Ergonomics

The shape of the handpiece neck portion has been redesigned in the handpiece of the invention to provide additional tooth clearance and better field of vision clearance. The neck portion of conventional handpieces is designed to provide a certain amount of tooth clearance. This is achieved by bending the forward end 17 of the neck portion 14 adjacent the head 16 away from the longitudinal axis of the handle 11 at a fixed angle of deflection. However, since the upwardly bent portion of the neck 14 is substantially straight, maximum tooth clearance is only achieved immediately behind the drive head 16. Furthermore, the maximum tooth clearance is limited by the length of the burr 80, since for ergonomic reasons the tip of the burr 80 must align with the longitudinal axis of the handpiece. This is required so that the angle of attack of the burr 80 on the tooth surface can be changed without movement of the burr tip by simply rotating the handle portion about the longitudinal axis of the handpiece (see FIG. 11b.

Figure 11A:
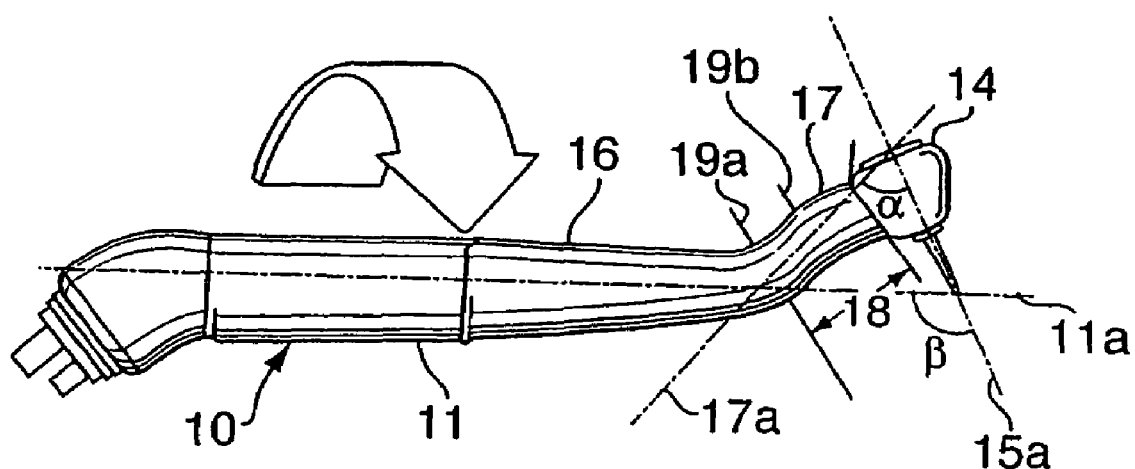
FIGS. 11 and 12 illustrate the ergonomics of a handpiece in accordance with the present invention.
Figure 11B:
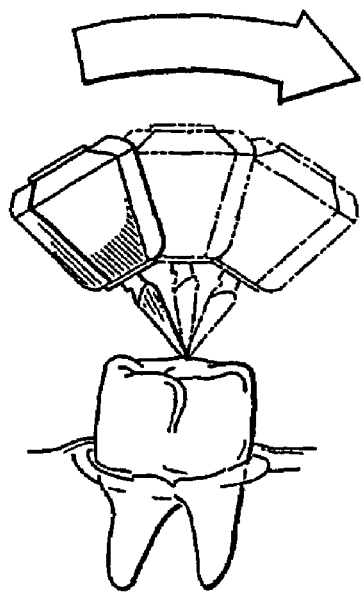
Figure 12:
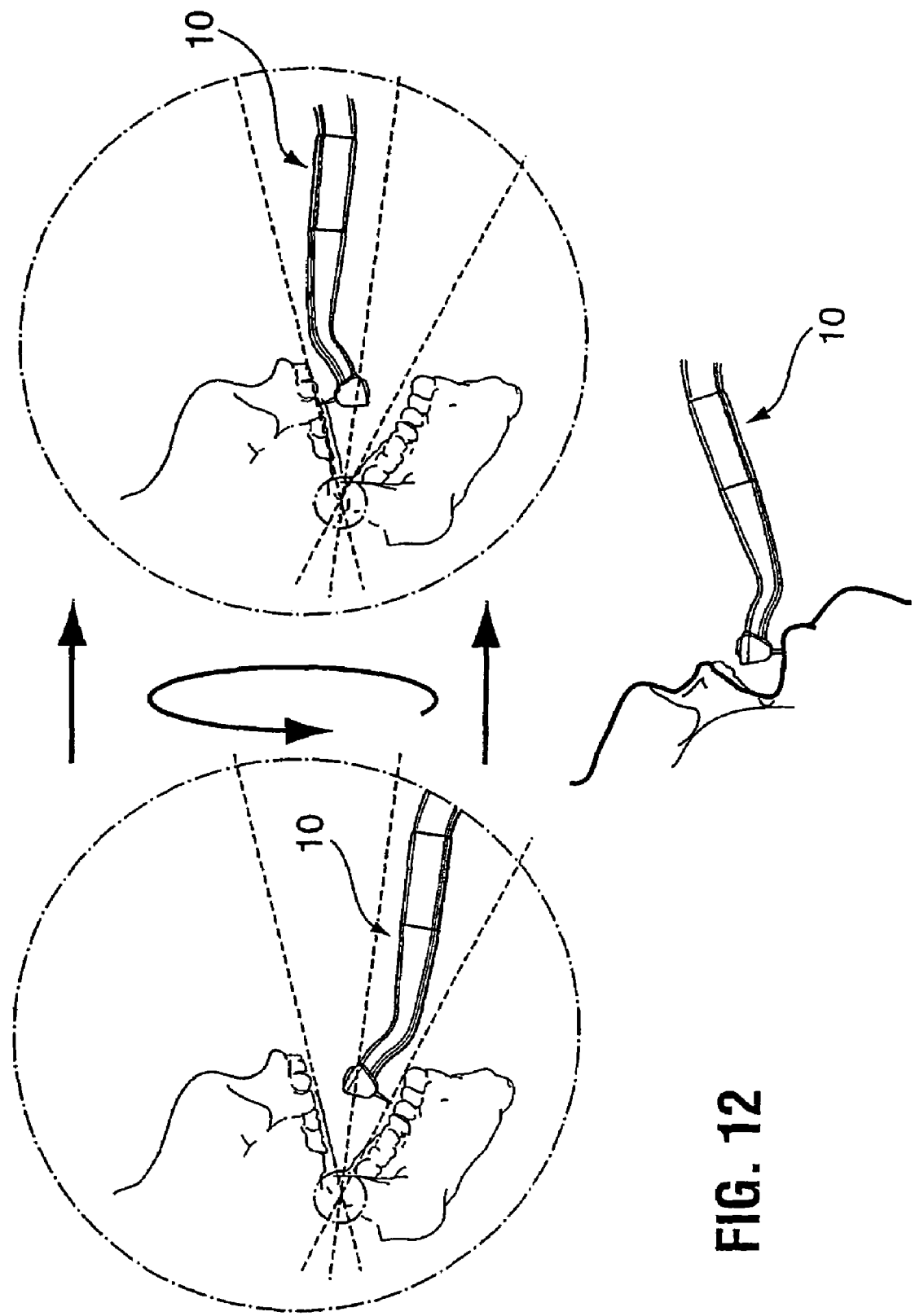

Additional clearance and a better field of vision is now achieved in the preferred embodiment of a handpiece in accordance with the invention (see FIGS. 11a, b and 12) in that the forward part 17 of the neck portion 16 has two different bend angles. The bent portion 18 includes a first portion 19 a adjacent the handle 11 which is bent away from the longitudinal axis 10a of the handpiece 10 at a much larger angle than in the prior art. The bent portion 18 further includes a second portion 19b which is bent in the opposite direction back towards the longitudinal axis 11a and therefore encloses an angle with the axis 10a which is much smaller than that of the first portion 19. In other words, the drive head 14 is mounted on the neck portion 17 in relation to the handle portion 11 in such a way that the tool axis 15a encloses an angle a of less than 90° with the longitudinal axis 17a of the neck portion 17 and an angle β of more than 90° with the longitudinal axis 11a of the handle portion 11, while the tip of the tool 15 coincides with the axis 11a. This construction provides a larger area of clearance between the bent portion 18 and the axis than in prior art designs. (see FIG. 12) At the same time, it is ensured that the tip of the burr is still aligned with the longitudinal axis. This alignment allows the dentist to adjust the angle of the burr relative to the tooth of a patient without changing the hand support position. Adjustment of the burr angle is achieved simply by rolling the handpiece between the fingers, similar to a pen as illustrated in FIG. 11b. The alignment of the burr with the handpiece axis prevents lateral displacement of the burr relative to the tooth as long as the handpiece is rotated about the longitudinal axis 11a of the handle as apparent from FIG. 11b.

Swivel Connector

As mentioned above, conventional handpiece designs include swivel connectors for connection of the handpiece to the umbilical cord and preventing twisting and kinking of the umbilical cord. The weight of the umbilical cord places a strain on the dentist's wrist. This is aggravated by the relatively stiff umbilical cord extending from the rear of the handpiece, which acts as a lever. That problem has now been addressed in the preferred embodiment of a handpiece in accordance with the invention (see FIGS. 8, 10, 11) in that the swivel connector is angled. Providing an angled swivel connection ensures that the umbilical cord always hangs more or less straight down from the handpiece so that the lever effect is overcome and the strain on the wrist significantly reduced. In the preferred embodiment shown in FIG. 11, the connector is constructed as a swivel connector 100 having an angled body 101 with a quick connect coupling arrangement at each end. The angled body provides a connection between the handle of the handpiece and the umbilical cord of less than 180 degrees. The first quick connect coupling 102 is designed to provide a rotatable swivel connection to the handpiece coaxial with the longitudinal axis of the handpiece, while the second quick connect coupling 103 provides a rotatable swivel connection of the connector body 101 to the umbilical cord (not shown). The angled connector can also be constructed as a retrofit connector for insertion in conventional swivel connection arrangements between the umbilical cord and the connector end of conventional handpieces. It will be readily apparent to the person skilled in the art that many different types of swivel connection structures can be used to achieve the rotatable connection between the connector body 101 and the handpiece, such as screw-on, snap-on or quick connect (bayonet) type connections commonly used in the art. Consequently, a discussion of the detailed construction of the swivel connection is not required, since the art skilled person will be able to choose one of the known swivel type connections for multiple conduits. In principle, any the prior art connecting structure allowing a sealed rotatable connection for multiple rigid pressurized conduits can be used.

Figure 13A:
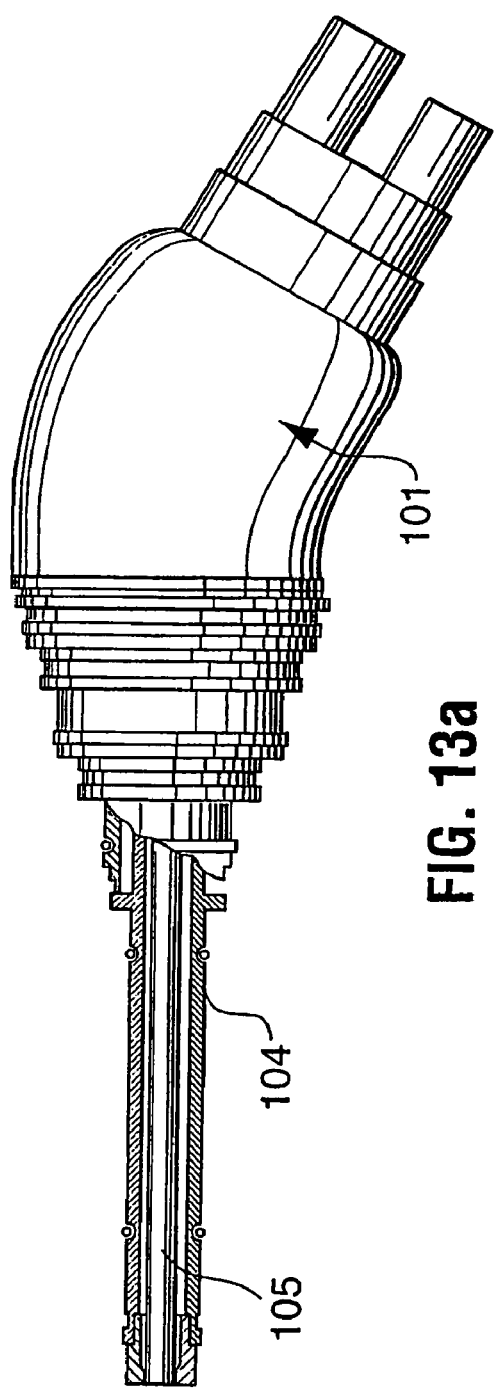
FIG. 13 illustrates the lighting system of one embodiment of a handpiece in accordance with the present invention.
Figure 13C:
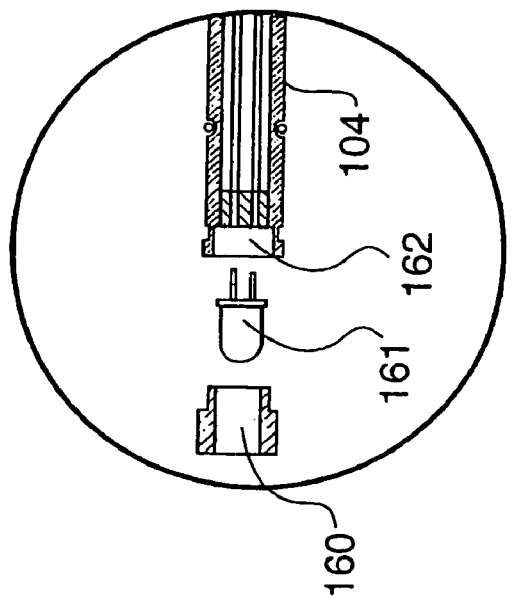
Figure 13B:
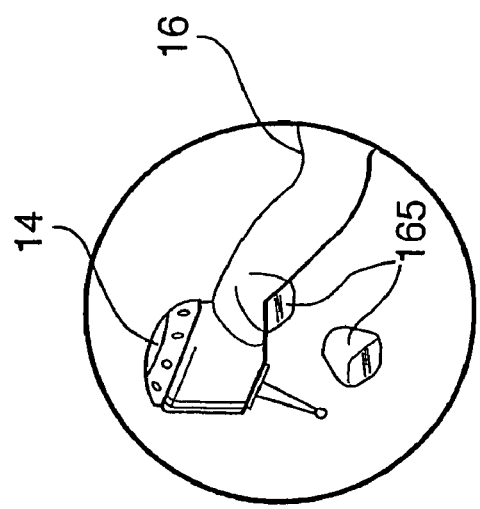

In the preferred embodiment of this invention, the swivel connector body 101 is directly fixed to the end of the umbilical cord and only has one swivel arrangement for connection with the handpiece (see FIG. 10). The connector body 101 also has a fiberoptic conduit extension 104, which isolates the fiberoptic line 105 from the turbine drive air, chip air/water and air exhaust conduits. This prevents contamination by oils (lubrication fluid for turbine and bearings) and fluids in supply lines, thereby maintaining the fiberoptic performance over a long service period. The fiberoptic conduit extension can also be modified to include light source at its end. This is achieved by incorporating into the free end of extension 104 an LED or light bulb socket 162 for receiving an LED or light bulb 61 as light source and a cover sleeve 160 for protecting the light source from damage during plugging and unplugging of the quick connection. In the preferred embodiment illustrated in FIG. 13b, light is supplied to the neck portion 16 of the handpiece by way of a fiberoptic waveguide and the end of the waveguide at the neck portion is covered with a protective lense cap 165, which is shaped curved retaining arms to tightly snap around the neck portion. The tense cap 165 is shown in the removed and installed condition.

The above-described embodiments of the present invention are intended to be examples only. Alterations, modifications and variations may be effected to the particular embodiments by those of skill in the art without departing from the scope of the invention, which is defined solely by the claims appended hereto.

The invention claimed is:

1. A medical or dental handpiece for use with a rotatable tool having a tool shaft for insertion into the handpiece and an axis of rotation, the tool shaft having a torque lock portion of non-circular cross-section having rotational symmetry, the handpiece comprising:
   a handle portion for gripping by a user;
   a drive head connected with the handle portion and forming a drive housing;
   a drive for generating torque, the drive rotatably supported in the drive housing for rotation about an axis of rotation, the drive having an axial bore; and
   a spindle received in the axial bore of the drive for transferring torque generated by the drive to the rotatable tool when inserted into the handpiece, the spindle having an axial tool bore for receiving the tool shaft, the spindle being connected to the drive for torque transmission, the spindle including a tool retaining arrangement for releasably retaining the tool shaft in the axial tool bore against axial movement upon insertion of the tool shaft into the axial tool bore, the spindle further including a torque lock independent of and axially spaced from the tool retaining arrangement and positioned concentrically in the axial tool bore of the spindle for concentrically receiving the torque lock portion of the tool shaft, the torque lock having at least a portion of non-circular cross-section adapted for engaging and locking at least a portion of the torque lock portion of the tool shaft to prevent rotation of the torque lock portion of the tool shaft in the torque lock, while permitting axial insertion of the torque lock portion of the tool shaft into the torque lock, the torque lock being connected to the spindle for rotation therewith.

2. The handpiece as defined in claim 1, wherein the torque lock is shaped and constructed for receiving the torque lock portion of the tool shaft having a triangular cross-section.

3. The handpiece of claim 1, wherein the torque lock has a bore for receiving the torque lock portion of the tool shaft and a torque transfer member, the torque transfer member being a protrusion extending radially inwardly into the bore for locking the torque lock portion of the tool shaft against rotation, while permitting axial insertion of the torque lock portion of the tool shaft into the torque lock.

4. The handpiece of claim 3, wherein a surface of the torque transfer member which engages the torque lock portion of the tool shaft during insertion of the tool shaft into the axial tool bore of the spindle has a rounded shape for automatically directing the torque lock portion of the tool shaft past the torque transfer member to achieve a self-alignment of the torque lock portion in the torque lock during insertion of the tool shaft.

5. The handpiece of claim 3, wherein the tool retaining arrangement includes a pair of complementary, interengaging elements respectively incorporated into the spindle and the tool shaft.

6. The handpiece as defined in claim 1, wherein the torque lock has a torque transfer member extending radially inwardly into the axial tool bore of the spindle for engagement of the torque lock portion of the tool shaft.

7. A torque transfer arrangement for a medical or dental handpiece having a drive for generating torque for rotatably driving a burr about an axis of rotation, the burr having an axis of rotation and a burr shaft with a torque lock portion of non-circular cross-section having rotational symmetry and the drive having an axial bore, the torque transfer arrangement comprising:
   a spindle to be received in the axial bore of the drive, the spindle having an axial tool bore for receiving the burr shaft, the spindle being connectable with the drive for torque transmission, the spindle further including a burr retaining arrangement for releasably retaining the burr shaft in the axial tool bore against axial movement upon insertion of the burr shaft into the axial tool bore; and
   a torque lock independent of and axially spaced from the burr retaining arrangement and positioned concentrically in the axial tool bore of the spindle for receiving the torque lock portion of the burr shaft, the torque lock having at least a portion of non-circular cross-section adapted for engaging and locking at least a portion of the torque lock portion of the burr shaft to prevent rotation of the burr shaft in the torque lock while permitting axial insertion of the torque lock portion of the burr shaft into the torque lock, the torque lock being connected to the spindle for rotation therewith.

8. The torque transfer arrangement of claim 7, wherein the cross-section of the torque lock portion of the burr shaft is triangular.

9. The torque transfer arrangement of claim 7, wherein the torque lock portion of the burr shaft is a terminal portion of the burr shaft and the torque lock has a bore for receiving the torque lock portion of the burr shaft and a torque transfer member protruding radially inwardly into the bore for preventing rotation of the torque lock portion of the burr shaft in relation to the spindle while permitting axial insertion of the burr shaft into the spindle.

10. The torque transfer arrangement of claim 9, wherein end surfaces of the torque transfer member and the terminal portion of the burr shaft which come into mutual contact during insertion of the burr shaft into the torque transfer arrangement have a rounded shape for directing the end surface of the terminal portion of the burr shaft past the torque transfer member to achieve a self-alignment of the terminal portion of the burr shaft relative to the torque transfer member during insertion of the burr shaft.

11. The torque transfer arrangement of claim 9, wherein the burr retaining arrangement includes a pair of complementary, interengaging structures respectively incorporated into the spindle and the burr shaft.

12. A medical or dental handpiece for use with a rotatable tool having a tool shaft for insertion into the handpiece and an axis of rotation, the tool shaft having a torque lock portion of non-circular cross-section having rotational symmetry, the handpiece comprising:
a handle portion for gripping by a user;
a drive head connected with the handle portion and forming a drive housing;
a drive for generating torque, the drive rotatably supported in the drive housing for rotation about an axis of rotation, the drive having an axial bore; and
a spindle received in the axial bore of the drive for transferring torque generated by the drive to the rotatable tool when inserted into the handpiece, the spindle having an axial tool bore for receiving the tool shaft, the spindle being connected to the drive for torque transmission, the spindle including a tool retaining arrangement for releasably retaining the rotatable tool in the axial tool bore against axial movement upon insertion of the tool shaft into the axial tool bore, wherein the tool retaining arrangement includes a pair of complementary, interengaging structures respectively incorporated into the spindle and the tool shaft, the spindle further including a torque lock independent of and axially spaced from the tool retaining arrangement and positioned concentrically in the axial tool bore of the spindle for concentrically receiving the torque lock portion of the tool shaft, the torque lock having at least a portion of non-circular cross-section adapted for engaging and locking at least a portion of the torque lock portion of the tool shaft to prevent rotation of the torque lock portion of the tool shaft in the torque lock, while permitting axial insertion of the torque lock portion of the tool shaft into the torque lock, the torque lock being connected to the spindle for rotation therewith.

13. The handpiece as defined in claim 1 or 12, wherein the drive is part of a drive unit including a turbine, a pair of axially spaced apart bearings for rotatably supporting the turbine in the drive housing and a chuck, the chuck including the spindle with the tool retaining arrangement and the torque lock.

14. A medical or dental handpiece for use with a rotatable tool having a tool shaft for insertion into the handpiece and an axis of rotation, the tool shaft having a torque lock portion of non-circular cross-section having rotational symmetry, the handpiece comprising:
a handle portion for gripping by a user;
a drive head connected with the handle portion and forming a drive unit housing; and
a drive unit for generating torque, the drive unit rotatably supported in the drive unit housing for rotation about the axis of rotation, the drive unit including a drive generating torque, a chuck for receiving the rotatable tool and for transferring torque generated by the drive to the rotatable tool when inserted into the handpiece, the chuck including a spindle having an axial tool bore for receiving the tool shaft, the spindle having a tool retaining arrangement for releasably and frictionally retaining the rotatable tool in the axial tool bore against axial movement upon insertion of the tool shaft into the axial tool bore, the spindle further including a torque lock independent of and axially spaced from the tool retaining arrangement and inserted concentrically into the axial tool bore of the spindle for concentrically receiving the torque lock portion of the tool shaft, the torque lock having at least a portion of non-circular cross-section adapted for engaging and locking at least a portion of the torque lock portion of the tool shaft to prevent rotation of the torque lock portion of the tool shaft in the torque lock, while permitting axial insertion of the torque lock portion of the tool shaft into the torque lock, the torque lock being connected to the spindle for rotation therewith.

15. The handpiece of claim 14, wherein the drive unit further includes a turbine and a pair of bearings for rotatably supporting the turbine in the drive unit housing, the turbine having an axial bore and the spindle being received in the axial bore of the turbine and connected to the turbine for torque transmission.

* * * * *